United States Patent
Pratap et al.

(10) Patent No.: US 7,807,712 B2
(45) Date of Patent: Oct. 5, 2010

(54) OXY SUBSTITUTED CHALCONES AS ANTIHYPERGLYCEMIC AND ANTIDYSLIPIDEMIC AGENTS

(76) Inventors: Ram Pratap, Central Drug Research Institute, Lucknow-226001 (IN); Mavurapu Satyanarayana, Central Drug Research Institute, Lucknow-226001 (IN); Chandeshwar Nath, Central Drug Research Institute, Lucknow-226001 (IN); Ram Raghubir, Central Drug Research Institute, Lucknow-226001 (IN); Anju Puri, Central Drug Research Institute, Lucknow-226001 (IN); Ramesh Chander, Central Drug Research Institute, Lucknow-226001 (IN); Priti Tiwari, Central Drug Research Institute, Lucknow-226001 (IN); Brajendra Kumar Tripathi, Central Drug Research Institute, Lucknow-226001 (IN); Arvind Kumar Srivastava, Central Drug Research Institute, Lucknow-226001 (IN)

( * ) Notice: Subject to any disclaimer, the term of this patent is extended or adjusted under 35 U.S.C. 154(b) by 0 days.

(21) Appl. No.: 11/018,923

(22) Filed: Dec. 22, 2004

(65) Prior Publication Data

US 2006/0142303 A1 Jun. 29, 2006

(51) Int. Cl.
*A61K 31/36* (2006.01)
*A61K 31/427* (2006.01)
*A61K 31/085* (2006.01)
*C07D 317/06* (2006.01)
*C07C 49/105* (2006.01)
*C07C 49/11* (2006.01)
*A61P 3/10* (2006.01)
*A61P 9/10* (2006.01)

(52) U.S. Cl. .................. 514/464; 514/369; 514/652; 549/434; 568/334

(58) Field of Classification Search .................. 568/334; 514/464, 369, 652; 549/434
See application file for complete search history.

(56) References Cited

OTHER PUBLICATIONS

Palanowski et. al., Acta Poloniae Pharmaceutica, 1967, 24(6), 567-574.*
Rastogi et. al., J. Med. Chem., 1972, 15(3), 286-291.*
Satyanarayana et. al., Bioorg. & Med. Chem., 2004, 12, 883-889.*

* cited by examiner

*Primary Examiner*—James O Wilson
*Assistant Examiner*—Susanna Moore
(74) *Attorney, Agent, or Firm*—The Nath Law Group

(57) ABSTRACT

The present invention provides appropriately substituted chalcones, such as, for example, represented by the structural formula as shown herein below

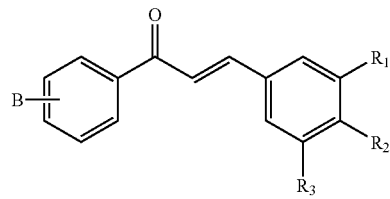

Wherein R1, R2 and R3 are selected from the group consisting of H, OH, O-alkyl, O-phenyl and O-substituted phenyl; B represents Ar—Z—O or RO; where Z is an alkane having up to 5 carbon atoms; R is substituted propanol amino, wherein substituted amino groups are selected from the group consisting of t-butyl, n-butyl, i-butyl, i-propyl, 4-phenyl piperazine-1-yl, 4-(2-methoxyphenyl)-piperazin-1-yl and 3,4-dimethoxy phenethyl; and Ar is thiazolidine-dione methylene phenoxy. The compounds prepared have been demonstrated to exhibit significant antidiabetic effect in various animal models indicating potential for further exploitation.

23 Claims, No Drawings

OXY SUBSTITUTED CHALCONES AS ANTIHYPERGLYCEMIC AND ANTIDYSLIPIDEMIC AGENTS

FIELD OF THE INVENTION

The present invention relates to synthesis of suitably substituted chalcone derivatives which exhibit pronounced antihyperglycemic activity in conjunction with antidyslipedemic activity. More particularly the invention relates to synthesis of compound having formula I and pharmaceutical composition containing these compounds, as described in the following description.

BACKGROUND OF THE INVENTION AND PRIOR ART

Type II diabetes mellitus accounts for 90-95% of all diabetes. Changed sedentary life style has contributed towards affliction of the disease to adult population also. The main force driving this increasing incidence is a staggering increase in obesity, the single most important contributor to the pathogenesis of diabetes mellitus. Prolonged disease condition leads to chronic macrovascular complications such as retinopathy and nephropathy. The disease is collectively referred, as metabolic syndrome encompasses type II diabetes and common constellation of closely linked clinical features. Characteristic factors include insulin resistance per se, obesity, hypertension and a common form of dyslipidemia and low high-density lipoprotein cholesterol. Metabolic syndrome is associated with marked increased incidence of coronary, cerebral and peripheral artery disease [Executive summary of the third report of the National Cholesterol Program Expert Panel on detection, evaluation and treatment of high blood cholesterol in adults (2001), J. Am. Med. Asso. 285, 2486-2496.].

The role of peripheral and hepatic insulin resistance in the pathogenesis of diabetes mellitus is undisputed. Insulin resistance can be due to multiple defects in signal transduction such as impaired activation of insulin receptor-tyrosine kinase and reduced activation of insulin-stimulated phosphatidyl inositol-3-hydroxy kinase. The resistance of insulin due to diet-induced obesity [Elchebly, M. et al. (1999), Science, 283, 1544.] has given the critical role of obesity in the development of insulin resistance and other features of the metabolic syndrome. Successful approaches attenuating appetite and/or enhancing energy expenditure will prove of great benefit in preventing and treating type H diabetes. Abnormalities of fatty acid metabolism are increasingly recognized as key components of the pathogenesis of the metabolic syndrome and type I diabetes. A critical player in potentiating the promoting effect of hyperinsulinaemia on hepatic lipid accumulation is the anabolic transcription factor SREBP-1, which upregulates genes such as that for fatty acid synthase [Shimomura, I. et al. (2000), Mol. Cell, 6, 77-86.]. These observations support a unified "lipotoxicity" hypothesis, which states that metabolic syndrome and type II diabetes can be caused by the accumulation of triglycerides and long chain fatty-acyl-CoA in liver and muscle. The third causal factor of metabolic syndrome is oxidative stress. Excess levels of oxygen in the living body can also pose a serious health threat; the so-called oxygen toxicity is brought about by oxygen species such as hydrogen peroxide and oxy radicals and damage living tissue. The active oxygen species are associated with diabetes mellitus and are destructive towards various tissues as occurring in diabetes mellitus. There have been many reports discussing relationships between peroxidation and diseases such as diabetes mellitus, atherosclerosis and myocardial ischemia in terms of radical oxidation. Glucose is oxidized under oxidative stress to highly reactive species, which ultimately reacts with proteins. Glucose, like other alpha hydroxy aldehydes, can enolize and thereby reduce molecular oxygen under physiological conditions, catalyzed by transition metals, yielding alpha keto aldehydes and oxidizing intermediates. These secondary compounds are more reactive than monosaccharides and can react with proteins to form cross-linked Maillard products (Simon P. Wolff et al. (1991); Free Radical Biology and Medicine, 10, 339-352.).

Oxidative stress also modifies lipids. Like glucose, LDL also undergoes oxidative modification to form modified LDL (oxidized LDL). The actual oxidation process is believed to begin with lipid peroxidation, followed by fragmentation to give short chain aldehydes. These aldehydes in turn react with the lysine residues of apo-B, creating a new epitope, which is recognized by the scavenger receptor of macrophages. During this same process, lecithin is converted to lysolecithin, which is a selective chemotactic agent for monocytes. The monocytes enter the subendothelium and undergo a phenotypic change to a macrophage, which avidly take up the oxidized LDL via the scavenger receptor. The uptake of oxidized LDL continues until the macrophage is so engorged with cholesteryl esters that it transforms into a foam cell. Groups of these foam cells constitute a fatty streak, the earliest hallmark of atherosclerosis. By inhibiting the oxidation of LDL, it is hoped that the modification of apo B and the production of chemotactic lysolecithin can be prevented and inturn the atherosclerosis.

At present, therapy for type II diabetes relies mainly on several approaches intended to reduce the hyperglycemia itself: sulphonylureas which increase insulin secretion from pancreatic beta cells; metformin which acts to reduce hepatic glucose production, peroxisome proliferator activated receptors agonists which enhance insulin action and α-glucosidase inhibitors which interfere with gut glucose absorption. These therapies have limited efficacy, limited tolerability and mechanism-based toxicity. Of particular concern is the tendency for most treatments to enhance weight gain. A problem particular to the sulphonylureas is that many patients who respond initially become refractory to treatment overtime.

The increasing prevalence of obesity and its associated comorbidities including type II diabetes and related cardiovascular disorders has stimulated efforts to develop effective new approaches in the treatment of this condition. While most therapeutic approaches involve altering the balance of metabolic energy by reducing energy intake, an alternative approach for the management of obesity is to affect an increase in the rate of energy expenditure. In 1984, compounds of the phenethanolamine class (as shown below), having thermogenic properties in rodents were first disclosed. Despite their structural similarity to known $\beta_1$ and $\beta_2$ adrenoceptor ligands, pharmacological studies indicated that these compounds stimulated a third or 'atypical' β-adrenergic receptor (β-AR) that is now described as $\ominus_3$-AR. $\beta_3$ agonist also increased insulin sensitivity and glucose utilization. Later studies suggested that Tyr 64 Arg $\beta_3$-AR mutation in the human population plays a role in the development of diabetes mellitus and/or obesity in some individuals possessing this genetic variant [Turner, N. C.; (1996), DDT, 1, 109-116].

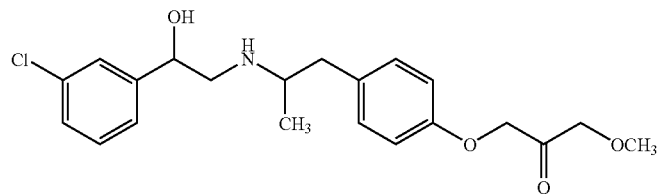

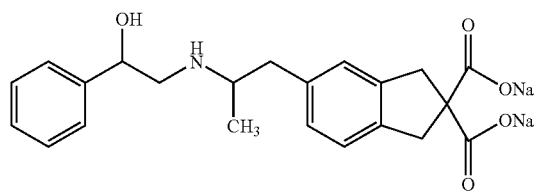

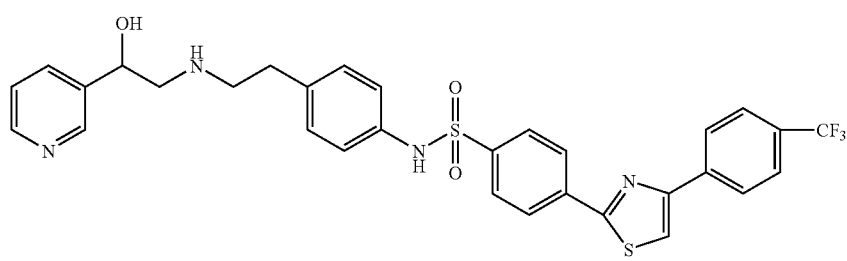

A family of transcription factors, known as PPAR-γ plays a crucial role in regulating the storage and catabolism of dietary energy producing materials. There are three PPAR subtypes that are the products of distinct genes and are commonly designated as PPPAR α, γ and δ. PPAR-γ affect body weight through regulation of fatty acid catabolism or energy expenditure. PPAR-γ expressed mainly in adipose tissue plays a pivotal role in regulation of glucose and lipid homeostasis [Willson, T. M. et al. (2000), J. Med. Chem. 43, 527-550].

Troglitazone effectively reduces hyperglycemia, hyperinsulinaemia and hypertriglyceridemia in patients with type II diabetes. The mechanism of pharmacological effects has been shown to involve increased insulin sensitivity effects in skeletal muscle, liver and adipose tissue via the activation of PPAR-γ. As vitamin-E analogue, troglitazone has been demonstrated to be an effective antioxidant; oxidative ring opening and subsequent quinone metabolite formation is believed to be the cause of hepatotoxicity and withdrawal of the drug [Kan He, et al. (2001), Biochemical Pharmacology, 62, 191-198.]. This has led to the modification and resulted in several new molecules.

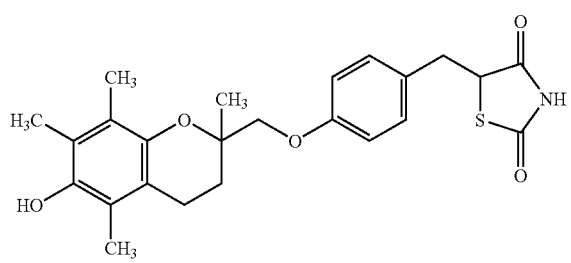

Troglitazone

-continued

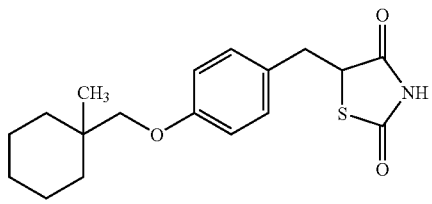

Ciglitzone

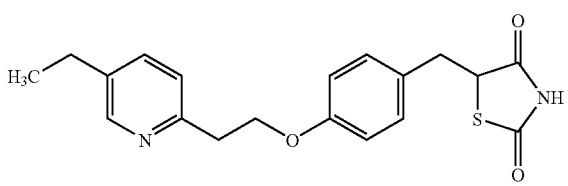

Pioglitazone

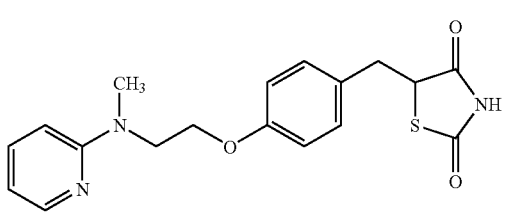

Rosiglitazone

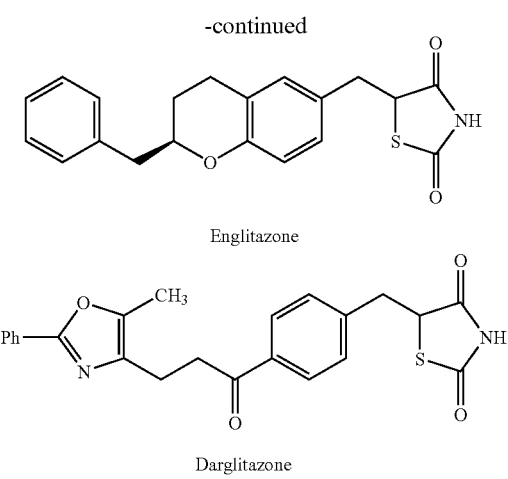

Englitazone

Darglitazone

Grafting of pharmacophores on systems own or very close metabolites may exhibit some times undesired effects. For example first generation of statins though derived from fungal metabolite, is very close analogue of mevalonic acid and therefore function as HMG-CoA reductase inhibitors, block mevalonate production which is involved in cholesterol biosynthesis and hence cholesterol synthesis is inhibited in the cell. Mevalonate is a common precursor for all isoprenoids such as ubiquinones (co enzyme Q 10), the dolichols, and isopentenyl tRNA etc. Therefore, there is a decrease in the synthesis of non-sterol constituents, which may contribute significantly to the side effects, observed with HMG-CoA reductase inhibitors. Similarly in designing of troglitazone, vitamin-E component was used which metabolized to quinonoid intermediate after one electron oxidation. This intermediate is speculated to be the cause of toxicity of troglitazone.

Flavonoids are among the most ubiquitous groups of polyphenolic compounds in foods of plant origin. Chalcones and flavones are among various subgroups of flavonoids. As integral constituents of the diet, they may exert a wide range of beneficial effects on human health. Flavonoids produce such biological effects through their free radical scavenging antioxidant activities and metal ion chelating abilities. (Cotelle, N. et al, Free Rad. Biol. Med. 1992, 13, 211.). These properties led us to utilize chalcones for the synthesis of hybrid molecules as antidiabetic and antidyslipidemic agents by substitution with thermogenic as well as insulin sensitizing pharmacophores.

OBJECTS OF THE PRESENT INVENTION

The main objective of the present invention is to provide a substituted chalcone derivative of formula I or a pharmaceutically acceptable salt thereof.

Another object of the present invention is to provide a pharmaceutical composition comprising these chalcone derivatives and a pharmaceutically acceptable carrier or diluent thereof.

Yet another object of the present invention is to provide a pharmaceutical composition comprising the chalcone derivatives of the present invention with a lipid lowering agent and a sugar lowering agent.

Still another object of the present invention is to provide a process for preparation of compound of formula I.

Yet another object of the present invention is to provide a method for controlling type II diabetes and associated hyperlipidemic conditions in a mammal by administering a pharmaceutically acceptable amount of compound I with or without other diabetic and lipid lowering agents.

Still another object of the present invention is to provide a method of controlling macrovascular conditions such as retinopathy and nephropathy in mammals by administering a pharmaceutically acceptable amount of the compound I with or without other diabetic and lipid lowering agents.

SUMMARY OF THE INVENTION

Accordingly, the present invention provides novel chalcone derivative of formula I which exhibit antihyperglycemic and antidyslipedemic activity. The invention also provides a method for controlling 'type II' diabetes and associated hyperlipidemic conditions in a mammal by administering composition containing these derivatives.

DETAILED DESCRIPTION OF THE INVENTION

The present invention provides novel chalcone derivatives, which exhibits antidiabetic and antidyslipidemic activities in different model systems. More particularly, this invention relates to compound having the formula I and pharmaceutically acceptable salts thereof. Where in the groups $R^1$, $R^2$ and $R^3$ are as herein after defined.

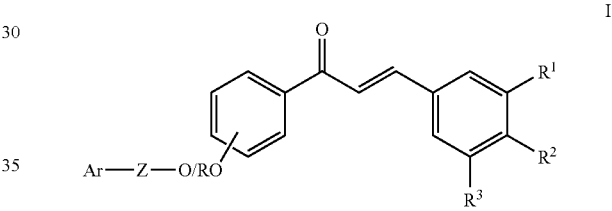

Wherein $R^1$, $R^2$ and $R^3$ are selected from H, OH, O-alkyl, O-phenyl, O-substituted phenyl or combination thereof;

Where Z is an alkane having up to 5 carbon atoms;

R is propanolamine wherein amino groups are selected from t-butyl amine, n-butyl amine, i-butyl amine, i-propyl amine, 4-phenyl piperazine-1-yl amine, 4-(2-methoxy phenyl)-piperazin-1-yl amine, and 3,4-dimethoxy phenethyl amine and Ar is thiazolidinedione methylene phenoxy Another embodiment of the present invention provides a pharmaceutical composition comprising the compound of formula I and pharmaceutically acceptable quantities of a conventional pharmaceutically acceptable carrier or diluent thereof.

Yet another embodiment of the present invention provides a pharmaceutical composition comprising the compound of formula I along with pharmaceutically acceptable quantities of conventional lipid lowering agents and/or conventional sugar lowering agents.

Yet another embodiment of the present invention provides a method for treating type II diabetes and associated hyperlipidemic conditions in mammals by administering a pharmaceutically effective amount of compound of formula I, optionally with other diabetic and lipid lowering agents.

Yet another embodiment of the present invention provides a method for treating type II diabetes and associated hyperlipidemic conditions in mammals by administering a pharmaceutically effective amount of compound of formula (18), optionally with other diabetic and lipid lowering agents.

Yet another embodiment of the present invention provides a method for treating type II diabetes and associated hyperlipidemic conditions in mammals by administering a pharmaceutically effective amount of compound of formula (34), optionally with other diabetic and lipid lowering agents.

Yet another embodiment of the present invention provides a method for treating type II diabetes and associated hyperlipidemic conditions in mammals by administering a pharmaceutically effective amount of compound of formula (46), optionally with other diabetic and lipid lowering agents.

Yet another embodiment of the present invention provides a method of treating macrovascular conditions such as retinopathy and nephropathy in mammals by administering a pharmaceutically effective amount of the compound of formula I, optionally with other diabetic and lipid lowering agents.

Yet another embodiment of the present invention provides a method of treating macrovascular conditions such as retinopathy and nephropathy in mammals by administering a pharmaceutically effective amount of the compound of formula (18), optionally with other diabetic and lipid lowering agents.

Yet another embodiment of the present invention provides a method of treating macrovascular conditions such as retinopathy and nephropathy in mammals by administering a pharmaceutically effective amount of the compound of formula (34), optionally with other diabetic and lipid lowering agents.

Yet another embodiment of the present invention provides a method of treating macrovascular conditions such as retinopathy and nephropathy in mammals by administering a pharmaceutically effective amount of the compound of formula (46), optionally with other diabetic and lipid lowering agents.

Yet another embodiment of the present invention provides the range of pharmaceutically effective dose of 50-200 mg/Kg body weight of the compound to be administered in mammals.

Still another embodiment of the present invention provides a compound of formula (18).

18

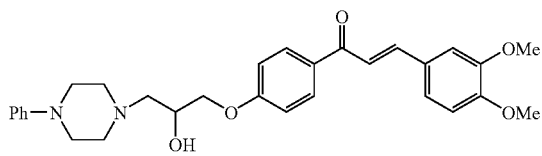

Yet another embodiment of the present invention provides a compound of formula (34)

34

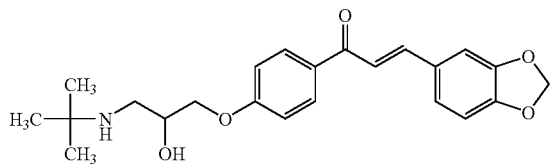

Yet another embodiment of the present invention provides a compound of formula (46)

46

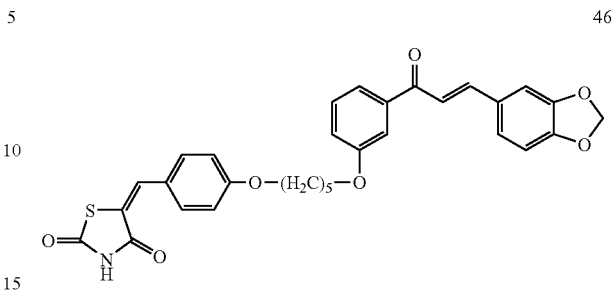

Still another embodiment of the present invention provides a process for preparing a compound of formula I, comprising the steps of:

(i) reacting hydroxy acetophenone and substituted benzaldehyde using aqueous sodium hydroxide in methanol at room temperature to obtain chalcones;

(ii) reacting chalcones obtained in step (i) with epichlorohydrin using sodium hydride as base in dry dimethyl formamide to obtain epoxide; and (iii) heating epoxide obtained in step (ii) under reflux at room temperature with suitable amines in methanol to yield corresponding propanolamines.

Yet another embodiment of the present invention provides a process for preparing a compound of formula I (43-46), comprising the steps of:

(i) reacting chalcone with dibromo alkane in presence of $K_2CO_3$ and acetone at room temperature to get bromo alkoxy chalcone; and (ii) reacting bromo alkoxy chalcone obtained in step (i) with 4-(Thiazolidin-2,4-dione-5-ylidinemethyl)-phenol, in presence of $K_2CO_3$ and dimethyl formamide at room temperature to obtain corresponding chalcone derived thiazolidinediones.

Synthesis of Chalcone Derived Propanolamines

All the chalcones [7-12] were prepared using the Claisen-Schmidt condensation, which has been previously reported (Sogawa, S.; Nihro, Y.; Ueda, H.; Izumi, A.; Miki, T.; Matsumosa, H.; Satoh, T. J. Med. Chem. 1993, 36, 3904). Hydroxy acetophenone [1-3] and appropriately substituted benzaldehyde [4-6] were reacted using aqueous sodium hydroxide in methanol at room temperature to provide corresponding chalcones [7-12]. Chalcones 10-12 were prepared under reflux. Yields ranged from 65% to quantitative. The chalcones were always obtained as transalkenes (E-form) as judged by $^1$H NMR spectroscopy. The chalcones thus obtained were reacted with epichlorohydrin using sodium hydride as base in dry dimethyl formamide. The purified epoxide [13-17] was heated under reflux with various amines in methanol to yield corresponding propanolamines [18-35] as presented in Scheme 1 (Table 1).

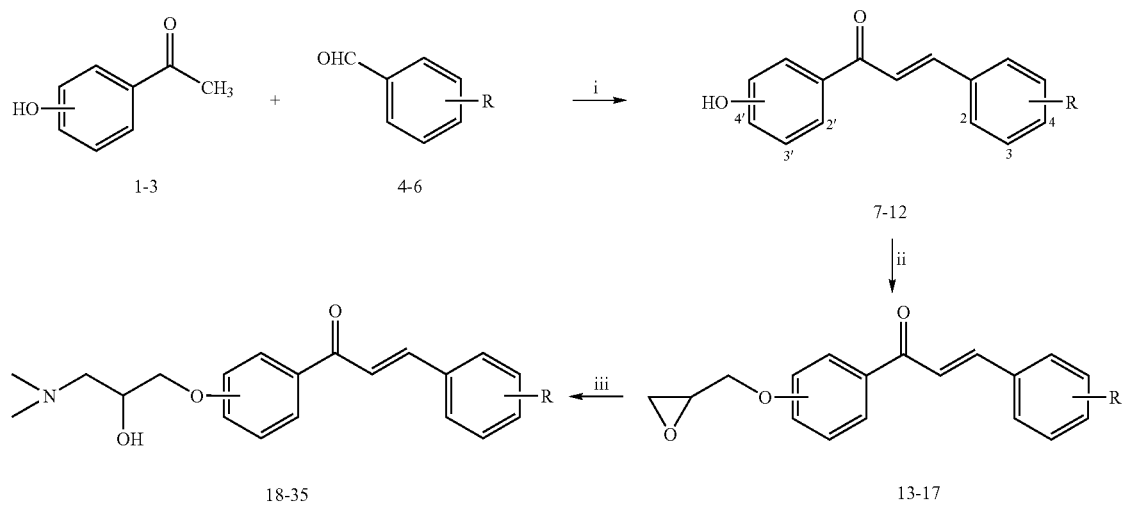

Scheme 1

Reagents and Conditions:
i 50% aq. NaOH, Methanol, RT
ii NaH, Epichlorohydrin, DMF, RT
iii Amine, Methanol, RT.

Synthesis of
4-(Thiazolidin-2,4-dione-5-ylidinemethyl)-Phenol 4-(Thiazolidin-2,4-dione-5-ylidinemethyl)-phenol (38) was synthesized by the condensation of 4-hydroxy benzaldehyde (36) with commercially available 2,4-thiazolidinedione (37) using piperidine as base in refluxing ethanol, according to a known procedure (Momose, Y.; Meguro, K.; Ikeda, H.; Hatanaka, C.; Oi, S.; Sohda, T. *Chem. Pharm. Bull.* 1991, 39, 1440.) (Scheme 2)

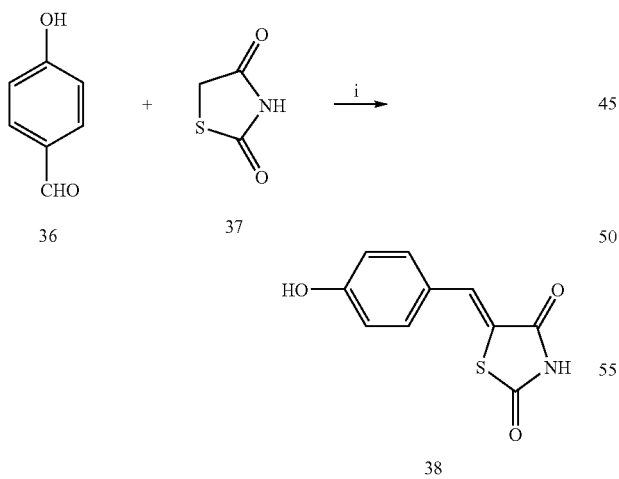

Scheme 2

Reagents and Conditions:
i Ethanol, Piperidine, Reflux.

Synthesis of Chalcone Derived Thiazolidinediones

Bromo alkoxy chalcone (39-42) were prepared by the reaction of chalcone (8&12) with dibromo alkane. Reaction of 38 with dibromo alkoxy chalcone in dry dimethyl formamide provided the target compounds (43-46). (Scheme 3, Table 2).

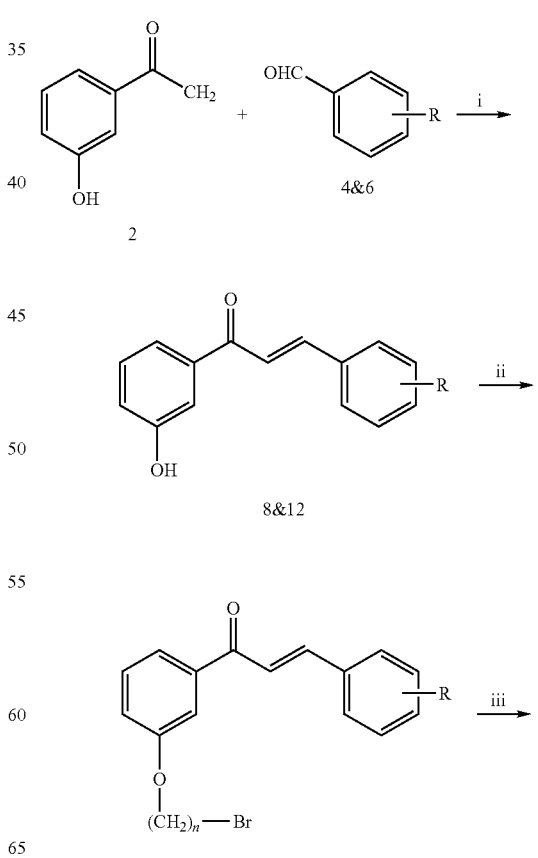

Scheme 3

-continued

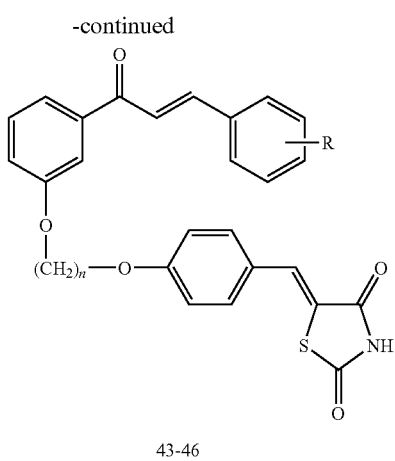

43-46

Reagents and Conditions:
i 50% aq. NaOH, Methanol, RT
ii Dibromo alkane, $K_2CO_3$, Acetone, RT
iii 38, $K_2CO_3$, DMF, RT.

TABLE 1

| Compd. No. | Position | R1,R2,R3 | Amine | Formula |
|---|---|---|---|---|
| 18 | 4' | 3,4-dimethoxy | 4-phenyl piperazine-1-yl | $C_{30}H_{34}N_2O_5$ |
| 19 | 4' | 3,4-dimethoxy | t-butyl | $C_{24}H_{31}NO_5$ |
| 20 | 4' | 4-methoxy | 4-phenyl piperazine-1-yl | $C_{29}H_{32}N_2O_4$ |
| 21 | 4' | 4-methoxy | i-butyl | $C_{23}H_{29}NO_4$ |
| 22 | 4' | 4-methoxy | t-butyl | $C_{23}H_{29}NO_4$ |
| 23 | 4' | 4-methoxy | i-propyl | $C_{22}H_{27}NO_4$ |
| 24 | 4' | 4-methoxy | 4-(2-methoxy phenyl)-piperzin-1-yl | $C_{30}H_{34}N_2O_5$ |
| 25 | 4' | 4-methoxy | 3,4-dimethoxy phenethyl | $C_{29}H_{33}NO_6$ |
| 26 | 4' | 4-methoxy | methyl | $C_{20}H_{23}NO_6$ |
| 27 | 4' | 4-methoxy | n-butyl | $C_{23}H_{29}NO_4$ |
| 28 | 3' | 4-methoxy | 4-phenyl piperazine-1-yl | $C_{29}H_{32}N_2O_4$ |
| 29 | 3' | 4-methoxy | i-propyl | $C_{22}H_{27}NO_4$ |
| 30 | 3' | 4-methoxy | t-butyl | $C_{23}H_{29}NO_4$ |
| 31 | 2' | 4-methoxy | n-butyl | $C_{23}H_{29}NO_4$ |
| 32 | 2' | 4-methoxy | i-propyl | $C_{22}H_{27}NO_4$ |
| 33 | 4' | 3,4-methylenedioxy | 4-phenyl piperazine-1-yl | $C_{29}H_{30}N_2O_5$ |
| 34 | 4' | 3,4-methylenedioxy | t-butyl | $C_{23}H_{27}NO_5$ |
| 35 | 4' | 3,4-methylenedioxy | i-butyl | $C_{23}H_{27}NO_5$ |

TABLE 2

| Compd. No. | n | R | Formula |
|---|---|---|---|
| 43 | 4 | 4-methoxy | $C_{30}H_{27}NO_6S$ |
| 44 | 5 | 4-methoxy | $C_{31}H_{29}NO_6S$ |
| 45 | 4 | 3,4-methylenedioxy | $C_{30}H_{25}NO_7S$ |
| 46 | 5 | 3,4-methylenedioxy | $C_{31}H_{27}NO_7S$ |

The invention is further elaborated with the help of following examples. However, these examples should not be construed to limit the scope of the invention.

EXAMPLES

4'-Hydroxy-4-methoxy-chalcone [7]

To a well-stirred solution of 4-hydroxy acetophenone, 1 (10 g, 73.5 mmol) and 4-methoxy benzaldehyde, 4 (8.9 mL, 73.5 mmol) in methanol (140 mL) was added 50% w/v aqueous sodium hydroxide solution (70 mL). The reaction mixture was stirred at room temperature for 12 h and then evaporated in vacuo. Water was added and acidified with hydrochloric acid (1N) and extracted with ethyl acetate. The organic layer was separated, washed with water, dried over sodium sulphate, filtered and evaporated in vacuo. The residue yielded pure 7 after purification by column chromatography. Yield 16.8 g (90%); mp 184-185° C. MS (EI) m/z 254 ($M^+$, 100%), 253 (34.7%), 239 (32.3%), 161 (36.8%), 121 (79.5%); IR (KBr) 3371, 1654; $^1$H NMR (200 MHz, $CDCl_3$) δ 7.99 (d, J=8.6 Hz, 2H), 7.78 (d, J=15.6 Hz, 1H), 7.60 (d, J=8.6 Hz, 2H), 7.41 (d, J=15.6 Hz, 1H), 6.93 (d, J=7.2 Hz, 4H), 5.85 (s, 1H), 3.86 (s, 3H).

3'-Hydroxy-4-methoxy-chalcone [8]

3-Hydroxy acetophenone, 2 (6.8 g, 50 mmol), 4-methoxy benzaldehyde, 4 (6.0 mL, 50 mmol) and 50% aqueous sodium hydroxide (50 mL) in methanol (110 mL) were reacted as in 7 to yield 8. Yield 12.5 g (98%); mp 93-94° C.; MS (FAB) 255 ($M^+$+1); IR (KBr) 3366, 1649; $^1$H NMR (200 MHz, $CDCl_3$) δ 7.80 (d, J=15.6 Hz, 1H), 7.62 (d, J=7.8 Hz, 1H), 7.58 (d, J=8.7 Hz, 2H), 7.55 (d, J=2.3 Hz, 1H), 7.38 (d, J=15.6 Hz, 1H), 7.36 (t, J=7.8 Hz, 1H), 7.04 (d, J=7.9 Hz, 1H), 6.92 (d, J=8.6 Hz, 2H), 3.85 (s, 3H).

2'-Hydroxy-4-methoxy-chalcone [9]

2-Hydroxy acetophenone, 3 (6 mL, 50 mmol), 4-methoxy benzaldehyde, 4 (6 mL, 50 mmol) and 50% aqueous sodium hydroxide (50 mL) in methanol (100 mL) were reacted as in 7 to yield 9. Yield 11.7 g (92%); mp 81-83° C. (lit. 93-94);[227] MS (FAB) 255 ($M^+$+1); IR (KBr) 3450, 1639; $^1$H NMR (200 MHz, $CDCl_3$) δ 7.92 (dd, J=8.7 Hz, 1.4 Hz, 1H), 7.90 (d, J=15.4 Hz, 1H), 7.62 (d, J=8.7 Hz, 2H), 7.53 (d, J=15.5 Hz, 1H), 7.49 (t, J=7.4 Hz, 1H), 6.95 (d, J=8.6 Hz, 2H), 7.03-6.89 (m, 2H), 3.86 (s, 3H).

3,4-Dimethoxy-4'-hydroxy-chalcone [10]

4-Hydroxy acetophenone, 1 (13.6 g, 100 mmol), 3,4-dimethoxy benzaldehyde, 5 (16.6 g, 100 mmol) and 50% aqueous sodium hydroxide (80 mL) in methanol (200 mL) were reacted under reflux as in 7 to yield 10. Yield 19.6 g (69%); mp 193-195° C.; MS (FAB) 285 ($M^+$+1); IR (KBr) 3443, 1643; $^1$H NMR (200 MHz, $CDCl_3$) δ 10.45 (s, 1H), 8.10 (d, J=8.5 Hz, 2H), 7.81 (d, J=15.5 Hz, 1H), 7.66 (d, J=15.5 Hz, 1H), 7.52 (s, 1H), 7.36 (d, J=8.2 Hz, 1H), 7.01 (d, J=8.4 Hz, 1H), 6.93 (d, J=8.5 Hz, 2H), 3.95 (s, 3H), 3.92 (s, 3H).

4'-Hydroxy-3,4-methylenedioxy-chalcone [11]

4-Hydroxy acetophenone, 1 (2.7 g, 20 mmol), 3,4-methylenedioxy benzaldehyde, 6 (3 g, 20 mmol) and 50% aqueous sodium hydroxide (5 mL) in methanol (40 mL) were reacted under reflux as in 7 to yield 11. Yield 3.5 g (65%); mp 191-193° C.; MS (FAB) 269 (M$^+$+1); IR (KBr) 3410, 1646; $^1$H NMR (200 MHz, CDCl$_3$) δ 9.15 (s, 1H), 7.98 (d, J=8.7 Hz, 2H), 7.72 (d, J=15.5 Hz, 1H), 7.37 (d, J=15.5 Hz, 1H), 7.16 (s, 1H), 7.12 (d, J=8.1 Hz, 1H), 6.99 (d, J=8.8 Hz, 2H), 6.82 (d, J=7.9 Hz, 1H), 6.02 (s, 2H).

3'-Hydroxy-3,4-methylenedioxy-chalcone [12]

3-Hydroxy acetophenone, 2 (2.7 g, 20 mmol), 3,4-methylenedioxy benzaldehyde, 6 (3 g, 20 mmol) and 50% aqueous sodium hydroxide (5 mL) in methanol (40 mL) were reacted under reflux as in 7 to yield 12. Yield 4.1 g (76%); mp 188-189° C.; MS (FAB) 269 (M$^+$+1); IR (KBr) 3389, 1659; $^1$H NMR (300 MHz, DMSO-d$_6$) δ 9.84 (s, 1H), 7.73 (d, J=15.6 Hz, 1H), 7.64 (d, J=15.9 Hz, 1H), 7.63 (s, 1H), 7.62 (d, J=5.4 Hz, 1H), 7.45 (s, 1H), 7.36 (t, J=7.9 Hz, 1H), 7.30 (d, J=7.8 Hz, 1H), 7.05 (dd, J=7.9 Hz, 2.4 Hz, 1H), 6.98 (d, J=7.8 Hz, 1H), 6.09 (s, 2H).

4'-(2,3-Epoxy-propoxy)-4-methoxy-chalcone [13]

To a well-stirred solution of 4'-hydroxy-4-methoxy-chalcone, 7 (15 g, 59 mmol) in dry dimethyl formamide (170 mL) was added 50% sodium hydride (5.6 g, 236 mmol) at 0-5° C. and after 30 minutes, excess of epichlorohydrin (13.8 mL, 177 mmol) was added and stirred at room temperature for overnight. The reaction mixture was concentrated under reduced pressure, diluted with water and extracted with chloroform. The combined organic layers were dried over sodium sulphate, filtered and evaporated to dryness. The crude product was purified by column chromatography to afford 13. Yield 11 g (60%); mp 85-87° C.; MS (FAB) 311 (M$^+$+1); IR (KBr) 1655; $^1$H NMR (200 MHz, CDCl$_3$) δ 8.02 (d, J=8.8 Hz, 2H), 7.77 (d, J=15.6 Hz, 1H), 7.59 (d, J=8.7 Hz, 2H), 7.41 (d, J=15.6 Hz, 1H), 6.99 (d, J=8.8 Hz, 2H), 6.93 (d, J=8.7 Hz, 2H), 4.32 (dd, J=11.1 Hz, 2.9 Hz, 1H), 4.01 (dd, J=11.1 Hz, 5.7 Hz, 1H), 3.84 (s, 31H), 3.40-3.35 (m, 1H), 2.92 (t, J=4.5 Hz, 4.5 Hz, 1H), 2.77 (dd, J=4.8 Hz, 2.6 Hz, 1H).

3'-(2,3-Epoxy-propoxy)-4-methoxy-chalcone [14]

By a similar procedure as described for 13, compound 14 was obtained from 3'-hydroxy-4-methoxy-chalcone, 8 (5 g, 19.7 mmol), epichlorohydrin (4.7 mL, 59 mmol) and 50% sodium hydride (2.83 g, 118 mmol) in dry dimethyl formamide (110 mL). Yield 4.6 g (75%); mp 64-65° C.; MS (FAB) 311 (M$^+$+1); IR (KBr) 1658; $^1$H NMR (200 MHz, CDCl$_3$) δ 7.79 (d, J=15.5 Hz, 1H), 7.60 (d, J=8.7 Hz, 1H), 7.60 (d, J=8.7 Hz, 2H), 7.56 (d, J=1.3 Hz, 1H), 7.41 (t, J=7.9 Hz, 1H), 7.39 (d, J=15.5 Hz, 1H), 7.15 (dd, J=8.1 Hz, 1.4 Hz, 1H), 6.94 (d, J=8.6 Hz, 2H), 4.34 (dd, J=11.0 Hz, 2.8 Hz, 1H), 4.01 (dd, J=11.0 Hz, 5.8 Hz, 1H), 3.86 (s, 3H), 3.40-3.38 (m, 1H), 2.93 (t, J=4.5 Hz, 4.4 Hz, 1H), 2.79 (dd, J=4.7 Hz, 2.6 Hz, 1H).

2'-(2,3-Epoxy-propoxy)-4-methoxy-chalcone [15]

By a similar procedure as described for 13, compound 15 was obtained from 2'-hydroxy-4-methoxy-chalcone, 9 (6 g, 23.6 mmol), epichlorohydrin (7.4 mL, 94.5 mmol) and 50% sodium hydride (2.76 g, 94.5 mmol) in dry dimethyl formamide (120 mL). Yield 3 g (42%); mp 57-58° C.; MS (FAB) 311 (M$^+$+1); IR (KBr) 1644; $^1$H NMR (200 MHz, CDCl$_3$) δ 7.64 (dd, J=8.5 Hz, 1.8 Hz, 1H), 7.63 (d, J=15.8 Hz, 1H), 7.60 (d, J=8.6 Hz, 2H), 7.45 (t, J=7.5 Hz, 1H), 7.34 (d, J=15.8 Hz, 1H), 7.10-6.95 (m, 2H), 6.92 (d, J=8.8 Hz, 2H), 4.36 (dd, J=1.0 Hz, 2.6 Hz, 1H), 4.08 (dd, J=11.0 Hz, 5.1 Hz, 1H), 3.84 (s, 3H), 3.34-3.31 (m, 1H), 2.85-2.77 (m, 2H).

3,4-Dimethoxy-4'-(2,3-epoxy-propoxy)-chalcone [16]

By a similar procedure as described for 13, compound 16 was obtained from 3,4-dimethoxy-4'-hydroxy-chalcone, 10 (14.2 g, 50 mmol), epichlorohydrin (7.8 mL, 100 mmol) and 50% sodium hydride (4.8 g, 200 mmol) in dry dimethyl formamide (150 mL). Yield 7 g (41%); mp 95-96° C.; MS (FAB) 341 (M$^+$+1); IR (KBr) 1655; $^1$H NMR (200 MHz, CDCl$_3$) δ 8.03 (d, J=8.8 Hz, 2H), 7.75 (d, J=15.5 Hz, 1H), 7.39 (d, J=15.5 Hz, 1H), 7.23 (dd, J=8.3 Hz, 1.5 Hz, 1H), 7.16 (s, 1H), 7.00 (d, J=8.8 Hz, 2H), 6.89 (d, J=8.3 Hz, 1H), 4.32 (dd, J=11.1 Hz, 2.9 Hz, 1H), 4.01 (dd, J=11.1 Hz, 5.8 Hz, 1H), 3.95 (s, 3H), 3.93 (s, 3H), 3.40-3.36 (m, 1H), 2.93 (t, J=4.5 Hz, 4.6 Hz, 1H), 2.79 (dd, J=4.8 Hz, 2.6 Hz, 1H).

4'-(2,3-Epoxy-propoxy)-3,4-methylenedioxy-chalcone [17]

By a similar procedure as described for 13, compound 17 was obtained from 4'-hydroxy-3,4-methylenedioxy-chalcone, 11 (6.4 g, 24 mmol), epichlorohydrin (5.6 mL, 72 mmol) and 50% sodium hydride (2.9 g, 120 mmol) in dry dimethyl formamide (120 mL). Yield 6.2 g (80%); mp 83-84° C.; MS (FAB) 325 (M$^+$+1); IR (KBr) 1650; $^1$H NMR (200 MHz, CDCl$_3$) δ 7.98 (d, J=8.8 Hz, 2H), 7.72 (d, J=15.5 Hz, 1H), 7.36 (d, J=15.5 Hz, 1H), 7.16 (s, 1H), 7.12 (d, J=8.1 Hz, 1H), 6.99 (d, J=8.8 Hz, 2H), 6.83 (d, J=7.9 Hz, 1H), 6.02 (s, 2H), 4.32 (dd, J=11.1 Hz, 3.0 Hz, 1H), 4.02 (dd, J=11.1 Hz, 5.7 Hz, 1H), 3.38-3.36 (m, 1H), 2.93 (t, J=4.4 Hz, 4.3 Hz, 1H), 2.78 (dd, J=4.8 Hz, 2.6 Hz, 1H).

3,4-Dimethoxy-4'-[2-hydroxy-3-(4-phenylpiperazin-1-yl)-propoxy]-chalcone [18]

A solution of 3,4-dimethoxy-4'-(2,3-epoxy-propoxy)-chalcone, 16 (1 g, 2.9 mmol) and 1-phenyl piperazine (0.45 mL, 3 mmol) in dry methanol (90 mL) was stirred at reflux for 6 h. Reaction mixture was concentrated on rotavapor and crude product purified by column chromatography to afford 18. Yield 870 mg (60%); mp 126-127° C.; MS (FAB) 503 (M$^+$+1); IR (KBr) 3426, 1652; $^1$H NMR (200 MHz, CDCl$_3$) δ 8.03 (d, J=8.8 Hz, 2H), 7.76 (d, J=15.5 Hz, 1H), 7.39 (d, J=15.5 Hz, 1H), 7.31-7.20 (m, 3H), 7.16 (d, J=1.3 Hz, 1H), 7.01 (d, J=8.8 Hz, 2H), 6.93 (d, J=7.8 Hz, 1H), 6.95-6.87 (m, 3H), 4.19-4.08 (m, 3H), 3.95 (s, 3H), 3.92 (s, 3H), 3.23 (t, J=4.7 Hz, 4H), 2.90-2.85 (m, 2H), 2.69-2.61 (m, 1H); $^{13}$C NMR (50 MHz, CDCl$_3$) δ 189.2, 162.8, 151.8, 151.6, 149.7, 144.6, 132.1, 131.1, 129.6, 128.5, 123.4, 120.3, 116.6, 114.8, 111.7, 110.7, 70.9, 65.9, 60.8, 56.5, 53.8, 49.7. Analyses calculated for C$_{30}$H$_{34}$N$_2$O$_5$: C, 71.69; H, 6.82; N, 5.57. Found: C, 71.18; H, 6.93; N, 5.32.

4'-[3-tert-Butylamino-2-hydroxy-propoxy]-3,4-dimethoxy-chalcone [19]

In a similar manner to the preparation of 18, compound 19 was obtained from 3,4-dimethoxy-4'-(2,3-epoxy-propoxy)-chalcone, 16 (1 g, 2.9 mmol) and tert-butyl amine (0.94 mL, 9 mmol) in dry methanol (80 mL). Yield 1.1 g (94%); mp 62-64° C.; MS (FAB) 414 (M$^+$+1); IR (KBr) 3450, 1650; $^1$H NMR (200 MHz, CDCl$_3$) δ 8.03 (d, J=8.8 Hz, 2H), 7.76 (d, J=15.5 Hz, 1H), 7.40 (d, J=15.5 Hz, 1H), 7.26 (s, 1H), 7.17 (dd, J=8.2 Hz, 1.6 Hz, 1H), 7.0 (d, J=8.8 Hz, 2H), 6.90 (d, J=8.3 Hz, 1H), 4.07-4.05 (m, 3H), 3.95 (s, 3H), 3.93 (s, 3H), 2.88 (dd, J=11.9 Hz, 4.0 Hz, 1H), 2.68 (dd, J=11.9 Hz, 7.5 Hz, 2H), 1.13 (s, 9H). Analyses calculated for $C_{24}H_{31}NO_5$: C, 69.71; H, 7.56; N, 3.39. Found: C, 69.82; H, 7.41; N, 3.16.

4'-[2-Hydroxy-3-(4-phenylpiperazin-1-yl)-propoxy]-4-methoxy-chalcone [20]

In a similar manner to the preparation of 18, compound 20 was obtained from 4'-(2,3-epoxy-propoxy)-4-methoxy-chalcone, 13 (1.3 g, 4.2 mmol) and 1-phenyl piperazine (0.64 mL, 4.2 mmol) in dry methanol (120 mL). Yield 1.4 g (70%); mp 165-167° C.; MS (FAB) 473 ($M^+$+1); IR (KBr) 3392, 1652; $^1$H NMR (200 MHz, $CDCl_3$) δ 8.03 (d, J=8.8 Hz, 2H), 7.78 (d, J=15.6 Hz, 1H), 7.60 (d, J=8.6 Hz, 2H), 7.42 (d, J=15.5 Hz, 1H), 7.31-7.24 (m, 2H), 7.01 (d, J=8.7 Hz, 2H), 6.94 (d, J=8.7 Hz, 2H), 6.96-6.84 (m, 3H), 4.19-4.09 (m, 3H), 3.86 (s, 3H), 3.24 (t, J=4.9 Hz, 4H), 2.89-2.84 (m, 2H), 2.74-2.64 (m, 4H). Analyses calculated for $C_{29}H_{32}N_2O_4$: C, 73.70; H, 6.83; N, 5.93. Found: C, 73.32; H, 6.41; N, 5.69.

4'-[3-iso-Butylamino-2-hydroxy-propoxy]-4-methoxy-chalcone [21]

In a similar manner to the preparation of 18, compound 21 was obtained from 4'-(2,3-epoxy-propoxy)-4-methoxy-chalcone, 13 (1 g, 3.2 mmol) and iso-butyl amine (1.6 mL, 16 mmol) in dry methanol (100 mL). Yield 900 mg (74%); mp 76-77° C.; MS (FAB) 384 ($M^+$+1); IR (KBr) 3423, 1653; $^1$H NMR (200 MHz, $CDCl_3$) δ 8.02 (d, J=8.6 Hz, 2H), 7.78 (d, J=15.6 Hz, 1H), 7.60 (d, J=8.5 Hz, 2H), 7.42 (d, J=15.6 Hz, 1H), 6.99 (d, J=8.8 Hz, 2H), 6.93 (d, J=8.6 Hz, 2H), 4.21-3.97 (m, 3H), 3.85 (s, 3H), 2.91-2.72 (m, 2H), 2.48 (d, J=6.7 Hz, 2H), 1.83-1.66 (m, 1H), 0.93 (d, J=6.6 Hz, 6H). Analyses calculated for $C_{23}H_{29}NO_4$: C, 72.04; H, 7.62; N, 3.65. Found: C, 72.12; H, 7.43; N, 3.52.

4'-[3-tert-Butylamino-2-hydroxy-propoxy]-4-methoxy-chalcone [22]

In a similar manner to the preparation of 18, compound 22 was obtained from 4'-(2,3-epoxy-propoxy)-4-methoxy-chalcone, 13 (1 g, 3.2 mmol) and tert-butyl amine (1.67 mL, 16 mmol) in dry methanol (80 mL). Yield 1 g (85%); mp 70-71° C.; MS (FAB) 384 ($M^+$+1); IR (KBr) 3391, 1640; $^1$H NMR (200 MHz, $CDCl_3$) δ 8.02 (d, J=8.7 Hz, 2H), 7.78 (d, J=15.7 Hz, 1H), 7.60 (d, J=8.7 Hz, 2H), 7.41 (d, J=15.6 Hz, 1H), 6.99 (d, J=8.9 Hz, 2H), 6.93 (d, J=8.7 Hz, 2H), 4.13-4.05 (m, 3H), 3.86 (s, 3H), 2.95-2.73 (m, 2H), 1.21 (s, 9H). Analyses calculated for $C_{23}H_{29}NO_4$: C, 72.04 H, 7.62; N, 3.65. Found: C, 72.09; H, 7.13; N, 3.72.

4'-[2-Hydroxy-3-iso-propylamino-propoxy]-4-methoxy-chalcone [23]

In a similar manner to the preparation of 18, compound 23 was obtained from 4'-(2,3-epoxy-propoxy)-4-methoxy-chalcone, 13 (1 g, 3.2 mmol) and iso-propyl amine (1.36 mL, 16 mmol) in dry methanol (100 mL). Yield 700 mg (59%); mp 105-106° C.; MS (FAB) 370 ($M^+$+1); IR (KBr) 3420, 3289, 1654; $^1$H NMR (200 MHz, $CDCl_3$) δ 8.02 (d, J=8.6 Hz, 2H), 7.78 (d, J=15.7 Hz, 1H), 7.60 (d, J=8.5 Hz, 2H), 7.42 (d, J=15.6 Hz, 1H), 6.99 (d, J=8.9 Hz, 2H), 6.93 (d, J=8.7 Hz, 2H), 4.23-4.09 (m, 3H), 3.85 (s, 3H), 2.96-2.74 (m, 3H), 1.11 (d, J=6.2 Hz, 6H). Analyses calculated for $C_{22}H_{27}NO_4$: C, 71.52; H, 7.37; N, 3.79. Found: C, 71.33; H, 7.42; N, 3.63.

4'-[2-Hydroxy-3-{4-(2-methoxyphenyl)-piperazin-1-yl}-propoxy]-4-methoxy-chalcone [24]

In a similar manner to the preparation of 18, compound 24 was obtained from 4'-(2,3-epoxy-propoxy)-4-methoxy-chalcone, 13 (500 mg, 1.6 mmol) and 1-(2-methoxyphenyl)piperazine (0.3 mL, 1.7 mmol) in dry methanol (80 mL). Yield 530 mg (66%); mp 97-98° C.; MS (FAB) 503 ($M^+$+1); IR (KBr) 3451, 1652; $^1$H NMR (200 MHz, $CDCl_3$) δ 8.03 (d, J=8.3 Hz, 2H), 7.78 (d, J=15.5 Hz, 1H), 7.60 (d, J=8.1 Hz, 2H), 7.43 (d, J=15.4 Hz, 1H), 7.03-6.85 (m, 8H), 4.13-4.09 (m, 3H), 3.87 (s, 3H), 3.86 (s, 3H), 3.14-3.10 (m, 4H), 2.90-2.88 (m, 2H), 2.67-2.63 (m, 4H). Analyses calculated for $C_{30}H_{34}N_2O_5$: C, 71.69; H, 6.82; N, 5.57. Found: C, 71.62; H, 6.91; N, 5.42.

4'-[3-{2-(3,4-Dimethoxyphenyl)-ethylamino}-2-hydroxy-propoxy]-4-methoxy-chalcone [25]

In a similar manner to the preparation of 18, compound 25 was obtained from 4'-(2,3-epoxy-propoxy)-4-methoxy-chalcone, 13 (1 g, 3.2 mmol) and 3,4-dimethoxyphenethylamine (2.65 mL, 16 mmol) in dry methanol (80 mL). Yield 930 mg (59%); mp 120-121° C.; MS (FAB) 492 ($M^+$+1); IR (KBr) 3431, 1654; $^1$H NMR (200 MHz, $CDCl_3$) δ 8.01 (d, J=8.8 Hz, 2H), 7.78 (d, J=15.6 Hz, 1H), 7.60 (d, J=8.7 Hz, 2H), 7.42 (d, J=15.5 Hz, 1H), 6.97 (d, J=8.6 Hz, 2H), 6.93 (d, J=9.1 Hz, 2H), 6.78-6.73 (m, 3H), 4.09-4.01 (m, 3H), 3.87 (s, 3H), 3.85 (s, 6H), 2.91-2.77 (m, 6H). Analyses calculated for $C_{29}H_{33}NO_6$: C, 70.86; H, 6.77; N, 2.85. Found: C, 70.81; H, 6.72; N, 2.91.

4'-[2-Hydroxy-3-methylamino-propoxy]-4-methoxy-chalcone [26]

In a similar manner to the preparation of 18, compound 26 was obtained from 4'-(2,3-epoxy-propoxy)-4-methoxy-chalcone, 13 (1 g, 3.2 mmol) and methylamine (5.5 mL, 64 mmol) in dry methanol (80 mL). Yield 470 mg (43%); mp 114-115° C.; MS (FAB) 342 ($M^+$+1); IR (KBr) 3487, 3344, 1652; $^1$H NMR (200 MHz, $CDCl_3$) δ 8.01 (d, J=8.6 Hz, 2H), 7.77 (d, J=15.6 Hz, 1H), 7.59 (d, J=8.5 Hz, 2H), 7.41 (d, J=15.6 Hz, 1H), 6.98 (d, J=8.9 Hz, 2H), 6.93 (d, J=8.7 Hz, 2H), 4.07-4.05 (m, 3H), 3.85 (s, 3H), 2.93-2.82 (m, 2H), 2.50 (s, 3H). Analyses calculated for $C_{20}H_{23}NO_4$: C, 70.36; H, 6.79; N, 4.10. Found: C, 70.40; H, 6.72; N, 4.13.

4'-[3-n-Butylamino-2-hydroxy-propoxy]-4-methoxy-chalcone [27]

In a similar manner to the preparation of 18, compound 27 was obtained from 4'-(2,3-epoxy-propoxy)-4-methoxy-chalcone, 13 (1 g, 3.2 mmol) and n-butyl amine (1.26 mL, 12.8 mmol) in dry methanol (100 mL). Yield 880 mg (72%); mp 163-164° C.; MS (FAB) 384 ($M^+$+1); IR (KBr) 3367, 1629; $^1$H NMR (200 MHz, $CDCl_3$) δ 8.02 (d, J=8.7 Hz, 2H), 7.77 (d, J=15.3 Hz, 1H), 7.59 (d, J=8.7 Hz, 2H), 7.41 (d, J=15.5 Hz, 1H), 6.99 (d, J=8.9 Hz, 2H), 6.93 (d, J=8.7 Hz, 2H), 4.20-3.95 (m, 3H), 3.86 (s, 3H), 2.93-2.55 (m, 2H), 2.55 (t, J=5.9 Hz, 2H), 1.57-1.39 (m, 4H), 0.93 (t, J=6.9 Hz, 3H). Analyses calculated for $C_{23}H_{29}NO_4$: C, 72.04; H, 7.62; N, 3.65. Found: C, 71.97; H, 7.58; N, 3.61.

3'-[2-Hydroxy-3-(4-phenylpiperazin-1-yl)-propoxy]-4-methoxy-chalcone [28]

In a similar manner to the preparation of 18, compound 28 was obtained from 3'-2,3-epoxy-propoxy)-4-methoxy-chalcone, 14 (500 mg, 1.6 mmol) and 1-phenyl piperazine (0.26 mL, 1.7 mmol) in dry methanol (75 mL). Yield 620 mg (82%); mp 153-154° C.; MS (FAB) 473 (M$^+$+1); IR (KBr) 3485, 1652; $^1$H NMR (200 MHz, CDCl$_3$) δ 7.79 (d, J=15.6 Hz, 1H), 7.60 (d, J=8.8 Hz, 1H), 7.60 (d, J=8.8 Hz, 2H), 7.58 (d, J=2.9 Hz, 1H), 7.41 (t, J=7.8 Hz, 1H), 7.39 (d, J=15.6 Hz, 1H), 7.31-7.23 (m, 2H), 7.16 (dd, J=8.1 Hz, 1.9 Hz, 2H), 6.94 (d, J=8.7 Hz, 2H), 6.96-6.83 (m, 2H), 4.19-4.08 (m, 3H), 3.86 (s, 3H), 3.23 (t, J=4.9 Hz, 4H), 2.89-2.81 (m, 2H), 2.70-2.62 (m, 4H). Analyses calculated for C$_{29}$H$_{32}$N$_2$O$_4$: C, 73.70; H, 6.83; N, 5.93. Found: C, 71.63; H, 6.54; N, 5.91.

3'-[2-Hydroxy-3-iso-propylamino-propoxy]-4-methoxy-chalcone [29]

In a similar manner to the preparation of 18, compound 29 was obtained from 3'-(2,3-epoxy-propoxy)-4-methoxy-chalcone, 14 (1 g, 3.2 mmol) and iso-propyl amine (1.36 mL, 16 mmol) in dry methanol (80 mL). Yield 910 mg (76%); mp 102-103° C.; MS (FAB) 370 (M$^+$+1); IR (KBr) 3391, 3131, 1650; $^1$H NMR (200 MHz, CDCl$_3$) δ 7.79 (d, J=15.7 Hz, 1H), 7.60 (d, J=8.6 Hz, 1H), 7.60 (d, J=8.6 Hz, 2H), 7.55 (d, J=1.9 Hz, 1H), 7.40 (t, J=7.9 Hz, 1H), 7.38 (d, J=15.6 Hz, 1H), 7.14 (dd, J=7.6 Hz, 1.6 Hz, 2H), 6.94 (d, J=8.7 Hz, 2H), 4.09-4.01 (m, 3H), 3.86 (s, 3H), 2.92-2.74 (m, 3H), 1.10 (d, J=6.2 Hz, 6H). Analyses calculated for C$_{22}$H$_{27}$NO$_4$: C, 71.52; H, 7.37; N, 3.79. Found: C, 71.13; H, 7.29; N, 3.81.

3'-[3-tert-Butylamino-2-hydroxy-propoxy]-4-methoxy-chalcone [30]

In a similar manner to the preparation of 18, compound 30 was obtained from 3'-(2,3-epoxy-propoxy)-4-methoxy-chalcone, 14 (1 g, 3.2 mmol) and tert-butyl amine (1.34 mL, 12.8 mmol) in dry methanol (120 mL). Yield 850 mg (69%); mp 83-84° C.; MS (FAB) 384 (M$^+$+1); IR (KBr) 3387, 1653; $^1$H NMR (200 MHz, CDCl$_3$) δ 7.78 (d, J=15.6 Hz, 1H), 7.60 (d, J=8.7 Hz, 1H), 7.60 (d, J=8.7 Hz, 2H), 7.56 (d, J=2.5 Hz, 1H), 7.40 (t, J=7.9 Hz, 1H), 7.38 (d, J=15.6 Hz, 1H), 7.14 (dd, J=7.6 Hz, 1.7 Hz, 1H), 6.94 (d, J=8.7 Hz, 2H), 4.09-4.01 (m, 3H), 3.86 (s, 3H), 2.92-2.81 (m, 3H), 1.14 (s, 9H). Analyses calculated for C$_{23}$H$_{29}$NO$_4$: C, 72.04; H, 7.62; N, 3.65. Found: C, 72.08; H, 7.57; N, 3.58.

2'-[3-n-Butylamino-2-hydroxy-propoxy]-4-methoxy-chalcone [31]

In a similar manner to the preparation of 18, compound 31 was obtained from 2'-(2,3-epoxy-propoxy)-4-methoxy-chalcone, 15 (450 mg, 1.45 mmol) and n-butyl amine (0.72 mL, 7.26 mmol) in dry methanol (70 mL). Yield 480 mg (86%); mp 106-107° C.; MS (FAB) 384 (M$^+$+1); IR (KBr) 3430, 3295, 1644; $^1$H NMR (200 MHz, CDCl$_3$) δ 7.60 (d, J=8.9 Hz, 1H), 7.58 (d, J=15.8 Hz, 1H), 7.56 (d, J=8.4 Hz, 2H) 7.45 (t, J=7.1 Hz, 1H), 7.28 (d, J=15.8 Hz, 1H), 7.08-7.01 (m, 2H), 6.91 (d, J=8.6 Hz, 2H), 4.15-4.04 (m, 3H), 3.84 (s, 3H), 2.84-2.68 (m, 2H), 2.52 (t, J=5.9 Hz, 2H), 1.40-1.25 (m, 4H), 0.87 (t, J=6.9 Hz, 3H). Analyses calculated for C$_{23}$H$_{29}$NO$_4$: C, 72.04; H, 7.62; N, 3.65. Found: C, 71.96; H, 7.57; N, 3.61.

2'-[2-Hydroxy-3-iso-propylamino-propoxy]-4-methoxy-chalcone [32]

In a similar manner to the preparation of 18, compound 32 was obtained from 2'-(2,3-epoxy-propoxy)-4-methoxy-chalcone, 15 (1 g, 3.2 mmol) and iso-propyl amine (1.6 mL, 19.3 mmol) in dry methanol (100 mL). Yield 870 mg (73%); mp 88-89° C.; MS (FAB) 370 (M$^+$+1); IR (KBr) 3450, 3284, 1645; $^1$H NMR (200 MHz, CDCl$_3$) δ 7.60 (d, J=8.9 Hz, 1H), 7.58 (d, J=15.6 Hz, 1H), 7.55 (d, J=8.4 Hz, 2H), 7.44 (t, J=7.5 Hz, 1H), 7.28 (d, J=15.8 Hz, 1H), 7.08-6.97 (m, 2H), 6.91 (d, J=8.6 Hz, 2H), 4.14-3.95 (m, 3H), 3.84 (s, 3H), 2.83-2.61 (m, 3H), 0.97 (d, J=6.0 Hz, 6H). Analyses calculated for C$_{22}$H$_{27}$NO$_4$: C, 71.52; H, 7.37; N, 3.79. Found: C, 71.48; H, 7.41; N, 3.71.

4'-[2-Hydroxy-3-(4-phenylpiperazin-1-yl)-propoxy]-3,4-methylenedioxy-chalcone [33]

In a similar manner to the preparation of 18, compound 33 was obtained from 4'-(2,3-epoxy-propoxy)-3,4-methylenedioxy-chalcone, 17 (500 mg, 1.5 mmol) and 1-phenyl piperazine (0.23 mL, 1.5 mmol) in dry methanol (60 mL). Yield 540 mg (72%); mp 153-154° C.; MS (FAB) 487 (M$^+$+1); IR (KBr) 3396, 1651; $^1$H NMR (200 MHz, CDCl$_3$) δ 8.02 (d, J=8.8 Hz, 2H), 7.71 (d, J=15.5 Hz, 1H), 7.38 (d, J=15.5 Hz, 1H), 7.27 (t, J=7.9 Hz, 2H), 7.16 (s, 1H), 7.12 (d, J=8.0 Hz, 1H), 7.01 (d, J=8.8 Hz, 2H), 6.97 (d, J=7.2 Hz, 1H), 6.91-6.82 (m, 3H), 6.02 (s, 2H), 4.17-4.09 (m, 3H), 3.23 (t, J=4.8 Hz, 4H), 2.89-2.81 (m, 2H), 2.69-2.62 (m, 4H). Analyses calculated for C$_{29}$H$_{30}$N$_2$O$_5$: C, 71.59; H, 6.21; N, 5.76. Found: C, 71.62; H, 6.30; N, 5.81.

4'-[$^3$-tert-Butylamino-2-hydroxy-propoxy]-3,4-methylenedioxy-chalcone [34]

In a similar manner to the preparation of 18, compound 34 was obtained from 4'-(2,3-epoxy-propoxy)-3,4-methylenedioxy-chalcone, 17 (1 g, 2.9 mmol) and tert-butyl amine (0.93 mL, 9 mmol) in dry methanol (80 mL). Yield 1 g (84%); mp 122-piperazine 124° C.; MS (FAB) 398 (M$^+$+1); IR (KBr) 3401, 1660; $^1$H NMR (300 MHz, CDCl$_3$) δ 8.00 (d, J=8.7 Hz, 2H), 7.71 (d, J=15.6 Hz, 1H), 7.37 (d, J=15.6 Hz, 1H), 7.16 (s, 1H), 7.11 (d, J=8.1 Hz, 1H), 6.99 (d, J=8.7 Hz, 2H), 6.83 (d, J=7.8 Hz, 1H), 6.01 (s, 2H), 4.07-3.98 (m, 3H), 2.87 (dd, J=12.0 Hz, 3.9 Hz, 3.3 Hz, 1H), 2.69 (dd, J=12.0 Hz, 7.5 Hz, 7.5 Hz, 1H), 2.42 (bs, OH, NH), 1.13 (s, 9H); $^{13}$C NMR (50 MHz, CDCl$_3$) δ 188.9, 162.9, 150.1, 148.8, 144.8, 131.9, 131.1, 129.9, 125.4, 120.3, 114.8, 109.0, 107.1, 101.9, 71.2, 68.9, 45.0, 29.4. Analyses calculated for C$_{23}$H$_{27}$NO$_5$: C, 69.50; H, 6.85; N, 3.52. Found: C, 68.84; H, 6.94; N, 3.42.

4'-[3-iso-Butylamino-2-hydroxy-propoxy]-3,4-methylenedioxy-chalcone [35]

In a similar manner to the preparation of 18, compound 35 was obtained from 4'-(2,3-epoxy-propoxy)-3,4-methylenedioxy-chalcone, 17 (1 g, 2.9 mmol) and iso-butyl amine (0.89 mL, 9 mmol) in dry methanol (100 mL). Yield 1 g (84%); mp 122-123° C.; MS (FAB) 398 (M$^+$+1); IR (KBr) 3325, 1657; $^1$H NMR (200 MHz, CDCl$_3$) δ 8.00 (d, J=8.8 Hz, 2H), 7.72 (d, J=15.5 Hz, 1H), 7.36 (d, J=15.5 Hz, 1H), 7.15 (s, 1H), 7.10 (dd, J=8.7 Hz, 1.3 Hz, 1H), 6.98 (d, J=8.8 Hz, 2H), 6.83 (d, J=7.9 Hz, 1H), 6.01 (s, 2H), 4.09-4.03 (m, 3H), 2.85-2.76 (m, 2H), 2.47 (d, J=6.5 Hz, 2H), 1.78-1.72 (m, 1H), 0.93 (d, J=6.6 Hz, 6H). Analyses calculated for C$_{23}$H$_{27}$NO$_5$: C, 69.50; H, 6.85; N, 3.52. Found: C, 69.53; H, 6.71; N, 3.14.

4-(Thiazolidin-2,4-dione-5-ylidinemethyl)-phenol (38)

A mixture of 4-hydroxy benzaldehyde, 36 (3 g, 24.6 mmol), 2,4-thiazolidinedione, 37 (2.9 g, 24.8 mmol), piperidine (2.5 mL) and methanol (100 mL) was refluxed for 18 h. The reaction mixture was poured into water and acidified with acetic acid to give 38, which was recrystallised from methanol. Yield 4.7 g (86%); mp 296-298° C.; MS (FAB) 222 ($M^+$+1); IR (KBr) 3404, 3123, 1723, 1678; $^1$H NMR (200 MHz, DMSO-$d_6$) δ 7.70 (s, 1H), 7.46 (d, J=8.6 Hz, 2H), 6.93 (d, J=8.6 Hz, 2H).

3'-(4-Bromo-butoxy)-4-methoxy-chalcone [39]

Potassium carbonate (2.2 g, 15.8 mmol) was added to a stirred solution of 3'-hydroxy-4-methoxy-chalcone, 8 (2 g, 7.87 mmol) in dry acetone (100 mL) at room temperature. After the mixture was stirred for 30 min, dibromo butane (4.7 mL, 39.4 mmol) was added and the resultant was stirred at room temperature for 12 h. Reaction mixture was filtered through celite, concentrated under reduced pressure and extracted with chloroform. The extract was washed with water, dried over sodium sulphate, filtered and concentrated in vacuo. The residue was purified by column chromatography to afford 39. Yield 2.8 g, (91%); mp 91-92° C.; MS (FAB) 389/391 ($M^+$+1); IR (KBr) 1654; $^1$H NMR (200 MHz, CDCl$_3$) δ 7.79 (d, J=15.6 Hz, 1H), 7.60 (d, J=8.7 Hz, 2H), 7.59 (d, J=7.6 Hz, 1H), 7.52 (d, J=2.0 Hz, 1H), 7.39 (t, J=7.8 Hz, 1H), 7.38 (d, J=15.6 Hz, 1H), 7.10 (dd, J=8.1 Hz, 2.3 Hz, 1H), 6.94 (d, J=8.7 Hz, 2H), 4.08 (t, J=5.7 Hz, 2H), 3.86 (s, 3H), 3.50 (t, J=6.3 Hz, 2H), 2.16-1.94 (m, 4H).

3'-(5-Bromo-pentyloxy)-4-methoxy-chalcone [40]

This compound (40) was prepared from 3'-hydroxy-4-methoxy-chalcone, 8 (2 g, 7.87 mmol), dibromo pentane (5.4 mL, 39.4 mmol) and potassium carbonate (2.2 g, 15.8 mmol) in dry acetone (100 mL) using the identical procedure as described for 39. Yield 2.7 g (85%); mp 83-84° C.; MS (FAB) 403/405 ($M^+$+1); IR (KBr) 1650; $^1$H NMR (200 MHz, CDCl$_3$) δ 7.78 (d, J=15.6 Hz, 1H), 7.60 (d, J=8.7 Hz, 2H), 7.58 (d, J=7.4 Hz, 1H), 7.52 (d, J=2.2 Hz, 1H), 7.39 (t, J=7.8 Hz, 1H), 7.39 (d, J=15.6 Hz, 1H), 7.10 (dd, J=8.0 Hz, 2.3 Hz, 1H), 6.93 (d, J=8.7 Hz, 2H), 4.04 (t, J=6.2 Hz, 2H), 3.85 (s, 3H), 3.44 (t, J=6.7 Hz, 2H), 1.99-1.81 (m, 4H), 1.71-1.60 (m, 2H).

3'-(4-Bromo-butoxy)-3,4-methylenedioxy-chalcone [41]

This compound (41) was prepared from 3'-hydroxy-3,4-methylenedioxy-chalcone, 12 (2.7 g, 10 mmol), dibromo butane (3.6 mL, 30 mmol) and potassium carbonate (2.76 g, 20 mmol) in dry acetone (100 mL) using the identical procedure as described for 39. Yield 3.6 g (89%); mp 97-98° C.; MS (FAB) 403/405 ($M^+$+1); IR (KBr) 1654; $^1$H NMR (200 MHz, CDCl$_3$) δ 7.73 (d, J=15.6 Hz, 1H), 7.58 (d, J=7.6 Hz, 1H), 7.51 (s, 1H), 7.39 (t, J=7.8 Hz, 1H), 7.34 (d, J=15.6 Hz, 1H), 7.16 (s, 1H), 7.14-7.07 (m, 2H), 6.84 (d, J=7.9 Hz, 1H), 6.02 (s, 2H), 4.07 (t, J=5.6 Hz, 2H), 3.50 (t, J=6.3 Hz, 2H), 2.16-1.94 (m, 4H).

3'-(5-Bromo-pentyloxy)-3,4-methylenedioxy-chalcone [42]

This compound (42) was prepared from 3'-hydroxy-3,4-methylenedioxy-chalcone, 12 (2.7 g, 10 mmol), dibromo pentane (4.1 mL, 30 mmol) and potassium carbonate (2.76 g, 20 mmol) in dry acetone (100 mL) using the identical procedure as described for 39. Yield 2.7 g (64%); mp 87-88° C.; MS (FAB) 417/419 ($M^+$+1); IR (KBr) 1652; $^1$H NMR (200 MHz, CDCl$_3$) δ 7.73 (d, J=15.6 Hz, 1H), 7.57 (d, J=7.6 Hz, 1H), 7.51 (d, J=2.1 Hz, 1H), 7.39 (t, J=7.8 Hz, 1H), 7.34 (d, J=15.6 Hz, 1H), 7.16 (s, 1H), 7.14-7.10 (m, 2H), 6.02 (s, 2H), 4.05 (t, J=6.2 Hz, 2H), 3.50 (t, J=6.7 Hz, 2H), 2.02-1.78 (m, 4H), 1.71-1.59 (m, 2H).

4-Methoxy-3'-{4-[4-(thiazolidin-2,4-dione-5-ylidinemethyl)-phenoxy]-butoxy}-chalcone [43]

A mixture of 3'-(4-bromo-butoxy)-4-methoxy-chalcone, 39 (1.2 g, 3.1 mmol), 4-(thiazolidin-2,4-dione-5-ylidinemethyl)-phenol, 38 (1 g, 4.62 mmol) and potassium carbonate (600 mg, 4.34 mmol) in dry dimethyl formamide (80 mL) was stirred at room temperature for 8 h. The reaction mixture was filtered through celite, diluted with water and acidified with dilute hydrochloric acid and filtered. The crude product was purified by column chromatography to yield 43. Yield 800 mg (49%); mp 186-187° C.; MS (FAB) 530 ($M^+$+1); IR (KBr) 3429, 1729, 1688, 1657; $^1$H NMR (200 MHz, DMSO-$d_6$) δ 8.33 (s, 1H), 7.88 (d, J=8.7 Hz, 2H), 7.81 (d, J=17.8 Hz, 1H), 7.75 (s, 1H), 7.75 (d, J=7.7 Hz, 1H), 7.62 (s, 1H), 7.56 (d, J=8.8 Hz, 2H), 7.54 (t, J=9.3 Hz, 1H), 7.49 (d, J=17.6 Hz, 1H), 7.25 (dd, J=7.9 Hz, 2.1 Hz, 1H), 7.12 (d, J=8.7 Hz, 2H), 7.03 (d, J=8.7 Hz, 2H), 4.16 (s, 4H), 3.84 (s, 3H), 1.94 (s, 4H), Analysis Calcd for $C_{30}H_{27}NO_6S$: C, 68.04; H, 5.14; N, 2.64; S, 6.05. Found: C, 68.25; H, 5.37; N, 2.69; S, 5.89.

4-Methoxy-3'-{5-[4-(thiazolidin-2,4-dione-5-ylidinemethyl)-phenoxy]-pentyloxy}-chalcone [44]

A mixture of 3'-(5-bromo-pentyloxy)-4-methoxy-chalcone, 40 (1.4 g, 3.47 mmol), 4-(thiazolidin-2,4-dione-5-ylidinemethyl)-phenol, 38 (800 mg, 3.62 mmol) and potassium carbonate (500 mg, 3.62 mmol) in dry dimethyl formamide (80 mL) were reacted in a similar way as described for 43 to yield 44. Yield 970 mg (52%); mp 182-183° C.; MS (FAB) 544 ($M^+$+1); IR (KBr) 3288, 1736, 1682, 1654; $^1$H NMR (200 MHz, DMSO-$d_6$) δ 7.75 (d, J=8.7 Hz, 2H), 7.67 (d, J=17.1 Hz, 1H), 7.63 (s, 1H), 7.61 (d, J=7.7 Hz, 1H), 7.47 (s, 1H), 7.43 (d, J=9.1 Hz, 2H), 7.40 (t, J=9.6 Hz, 1H), 7.36 (d, J=17.0 Hz, 1H), 7.11 (d, J=8.1 Hz, 1H), 6.98 (d, J=8.9 Hz, 2H), 6.92 (d, J=8.7 Hz, 2H), 3.96 (s, 4H), 3.72 (s, 3H), 1.71-1.33 (m, 6H). Analysis Calcd for $C_{31}H_{29}NO_6S$: C, 68.49; H, 5.38; N, 2.58; S, 5.90. Found: C, 68.37; H, 5.46; N, 2.67; S, 6.08.

3,4-Methylenedioxy-3'-{4-[4-(thiazolidin-2,4-dione-5-ylidinemethyl)-phenoxy]-butoxy}-chalcone [45]

A mixture of 3'-(4-bromo-butoxy)-3,4-methylenedioxy-chalcone, 41 (3 g, 7.44 mmol), 4-(thiazolidin-2,4-dione-5-ylidinemethyl)-phenol, 38 (1.8 g, 8.14 mmol) and potassium carbonate (2.2 g, 16 mmol) in dry dimethyl formamide (125 mL) were reacted in a similar way as described for 45. Yield 800 mg (20%); mp 173-175° C.; MS (FAB) 544 ($M^+$+1); IR (KBr) 3373, 1726, 1664; $^1$H NMR (200 MHz, DMSO-$d_6$) δ 10.39 (s, 1H), 7.84 (s, 1H), 7.77 (s, 1H), 7.73 (d, J=16.9 Hz, 1H), 7.70 (d, J=6.2 Hz, 1H), 7.62 (s, 1H), 7.50 (d, J=8.5 Hz, 2H), 7.48 (t, J=8.4 Hz, 1H), 7.48 (d, J=16.7 Hz, 1H), 7.34 (d, J=7.9 Hz, 1H), 7.23 (d, J=6.5 Hz, 1H), 7.00 (d, J=8.1 Hz, 1H), 6.94 (d, J=8.5 Hz, 2H), 6.12 (s, 2H), 4.10 (s, 2H), 3.75 (s, 2H), 1.78 (s, 4H). Analysis Calcd for $C_{30}H_{25}NO_7S$: C, 66.29; H, 4.64; N, 2.58; S, 5.90. Found: C, 66.35; H, 4.57; N, 2.34; S, 6.13.

3,4-Methylenedioxy-3'-{5-[4-(thiazolidin-2,4-dione-5-ylidinemethyl)-phenoxy]-pentyloxy}-chalcone [46]

A mixture of 3'-(5-bromo-pentyloxy)-3,4-methylenedioxy-chalcone, 42 (2.5 g, 5.9 mmol), 4-(thiazolidin-2,4-dione-5-ylidinemethyl)-phenol, 38 (1.6 g, 7.24 mmol) and potassium carbonate (2.2 g, 16 mmol) in dry dimethyl formamide (125 mL) were reacted in a similar way as described for 43 to yield 46. Yield 1.4 g (42%); mp 159-161° C.; MS (FAB) 558 ($M^+$+1); IR (KBr) 3316, 1736, 1679, 1655; $^1$H NMR (200 MHz, DMSO-$d_6$) δ 10.41 (s, 1H), 7.85 (s, 1H), 7.74 (d, J=16.7 Hz, 1H), 7.73 (s, 1H), 7.71 (d, J=5.4 Hz, 1H), 7.63 (s, 1H), 7.50 (d, J=8.9 Hz, 2H), 7.48 (t, J=8.9 Hz, 1H), 7.48 (d, J=17.9 Hz, 1H), 7.36 (d, J=7.9 Hz, 1H), 7.23 (d, J=5.9 Hz, 1H), 7.01 (d, J=8.2 Hz, 1H), 6.95 (d, J=8.4 Hz, 2H), 6.13 (s, 2H), 4.08 (t, J=5.7 Hz, 2H), 3.70 (t, J=6.6 Hz, 2H), 1.80-1.66 (m, 4H), 1.49-1.46 (m, 2H); $^{13}$C NMR δ 189.0, 167.9, 166.2, 160.5, 159.3, 149.9, 148.5, 144.5, 139.5, 133.8, 132.9, 130.2, 129.6, 126.4, 124.3, 121.2, 120.4, 119.6, 117.0, 116.7, 114.1, 108.9, 107.1, 102.0, 67.8, 41.7, 28.5, 27.3, 23.0. Analysis Calcd for $C_{31}H_{27}NO_7S$: C, 66.77; H, 4.88; N, 2.51; S, 5.75. Found: C, 66.96; H, 4.91; N, 2.40; S, 5.46.

Biological Screening

The biological screening of the synthesized compounds for antihyperglycemic and antidyslipidemic activities were carried out in Biochemistry Division, Central Drug Research Institute. Sucrose loaded rat model was used for primary screening followed by streptozotocin induced beta cell damaged diabetic model of Sprague Dawley strain male albino rat model. The compounds, which exhibited significant activity repeatedly in STZ model, were subjected to screen in db/db mice. The serum of the mice was also analyzed for lipid profile of the compounds exhibiting antihyperglycemic activity. All the compounds were also screened for antidyslipidemic activity in triton model.

Evaluation of Antihyperglycemic Activity

Sucrose Loaded Rat Model (SLM)

Male albino rats of Charles Foster/Wistar strain of average body weight 160±20 g were selected for this study. The blood glucose level of each animal was checked by glucometer using glucostrips (Boehringer Mannheim) after 16 h starvation. Animals showing blood glucose levels between 3.33 to 4.44 mM (60 to 80 mg/dl) were divided into groups of five to six animals in each. Animals of experimental group were administered suspension of the desired synthetic compound orally (made in 1.0% gum acacia) at a dose of 100-mg/kg-body weight. Animals of control group were given an equal amount of 1.0% gum acacia. A sucrose load (10.0 g/kg) was given to each animal orally exactly after 30 min post administration of the test sample/vehicle. Blood glucose profile of each rat was again determined at 30, 60, 90 and 120 min post administration of sucrose by glucometer. Food but not water was withheld from the cages during the course of experimentation. Quantitative glucose tolerance of each animal was calculated by Area Under Curve (AUC) method (Prism Software). Comparing the AUC of experimental and control groups determined the percentage antihyperglycemic activity. Statistical comparison was made by Dunnett's test.

Sucrose-Challenged Streptozotocin-Induced Diabetic Rats (STZ-S)

Male albino rats of Sprague Dawley strain of body weight 160±120 g were selected for this study. Streptozotocin (Sigma, USA) was dissolved in 100 mM citrate buffer pH 4.5 and calculated amount of the fresh solution was injected to overnight fasted rats (45 mg/kg) intraperitoneally. Blood glucose level was checked 48 h later by glucostrips and animals showing blood glucose values between 144 to 270 mg/dl (8 to 15 mM) were included in the experiment and termed diabetic. The diabetic animals were divided into groups consisting of five to six animals in each group. Animals of experimental groups were administered suspension of the desired test samples orally (made in 1.0% gum acacia) at a dose of 100-mg/kg-body weight. Animals of control group were given an equal amount of 1.0% gum acacia. A sucrose load of 2.5-g/kg body weight was given after 30 minutes of compound administration. After 30 minutes of post sucrose load blood glucose level was again checked by glucostrips at 30, 60, 90, 120, 180, 240, 300 min and at 24 h, respectively. Animals not found diabetic after 24 hours post treatment of the test sample were not considered and omitted from the calculations and termed as non-responders. The animals, which did not show any fall in blood glucose profile in a group while the others in that group, showed fall in blood glucose profile were also considered as non-responders. Food but not water was withheld from the cages during the experimentation. Comparing the AUC of experimental and control groups determined the percent antihyperglycemic activity. Statistical comparison between groups was made by Student's 't' test.

$$\% \text{ Antihyperglycemic Activity} = 100 - \frac{\text{Average blood glucose level of test substance treated group at test time}}{\text{Average blood glucose level of control group at test time}} \times 100$$

Evaluation of Antidyslipidemic Activity

Triton Model

Male Charles foster rats weighing 200-225 g were divided into control, hyperlipidemic and hyperlipidemic plus drug treated groups containing six animals in each group. Hyperlipidemia was induced by administration of triton WR-1339 (200 mg/kg i.p.). All animals were maintained on a special pellet diet and water ad libitum. Compounds and standard drug were macerated with 0.2% aqueous gum acacia suspension. The suspension was fed orally at the dose of 100 mg/kg simultaneously with triton in drug treated group. The animals of control group received the same amount of gum acacia by similar route of administration. At the end of the experiment, after 18 h, blood was withdrawn from retro orbital plexus and plasma was used for the assay of total cholesterol, phospholipid and triglycerides.

Lipid Estimation

Cholesterol

Cholesterol was estimated using the kit provided by Roche Diagnostics. Cholesterol esters are enzymatically hydrolyzed by cholesterol esterase (CE) to cholesterol and free fatty acids. Free cholesterol, including that originally present, is then oxidized by cholesterol oxidase (CO) to cholest-4-en-3-one and hydrogen peroxide. The hydrogen peroxide combines with hydroxy benzoic acid (HBA) and 4-aminoantipyrine (4AAA) in the presence of peroxidase (POD) to form a chromophore (quinoneimine dye), which may be quantitated at 500-505 nm. The intensity of red colour formed is directly proportional to the concentration of total cholesterol in the specimen and measured spectrophotometrically (Searcy, C. L. Diagnostic Biochemistry, 1969, McGraw Hill, New York; Ellefson, R. D.; Caraway, W. T. Fundamentals of clinical chemistry, 1976, Ed Tietz N W, 506-515.)

Triglycerides

Triglycerides were estimated using the kit provided by Roche Diagnostics. Lipoprotein lipase hydrolyses triglycerides to yield glycerol and fatty acids. Glycerol kinase converts glycerol to glycerol-3-phosphate, which is oxidized by glycerol phosphate oxidase to dihydroxy acetone phosphate and hydrogen peroxide. In the presence of peroxidase, hydrogen peroxide oxidatively couples with 4-aminoantipyrine and 4-chloro phenol to produce red quinonimine dye. The intensity of red colour formed is directly proportional to the concentration of triglycerides in the specimen and is measured by photometrically (Wahlefeld, A. W.; Bergmeyer, H. U. Ed. Methods of enzymatic analysis, $2^{nd}$ English edition, New York, N.Y., Academic press inc, 1831-1840.).

Phospholipids

Serum (0.2 mL) and perchloric acid (1.0 mL) was digested at 180° C. for 1-1.5 h till the solution became colorless. The liberated inorganic phosphate (Pi) was measured by the method of Fiske and Subbarow (Fiske, C. H.; Subbarow, V. *J. Biol. Chem.* 1925, 66, 375.). 1 mL of 2.5% ammonium molybdate (prepared in 5 N sulphuric acid) and 0.5 mL reducing agent (4-amino naphthol sulphonic acid, 0.2%), sodium metabisulphite (2.4% w/v in distilled water) was added to the above tubes and mixed well. The reaction mixture was distilled with 2.5 mL of triple distilled water and kept at 60° C. in water bath for 20 min. For standard, an appropriate amount of potassium dihydrogen phosphate dissolved in triple distilled water containing 2-10 μg phosphorus (Pi) was run simultaneously with the experiment tubes. The optical density of the blue colour was recorded at 620 nm against reagent blank. The values of Pi were converted into phospholipid by multiplying with 25 (a constant calibrated from Pi value of lecithin).

TABLE 3

Antihyperglycemic and antidyslipidemic activity in SLM, STZ-S and triton models

| Compd. No. | % Fall in blood glucose levels (SLM&STZ-S models) | | | % Fall in lipid levels (Triton model) | | |
|---|---|---|---|---|---|---|
| | SLM | STZ-S 5 h | STZ-S 24 h | TC | PL | TG |
| 18 | 15.4 | — | 20.3 | 20 | 08 | 12 |
| 19 | 11.2 | NIL | NIL | 21 | 22 | 19 |
| 20 | 7.78 | NIL | NIL | 11 | 11 | 10 |
| 21 | 5.67 | ND | ND | 05 | 14 | 12 |
| 22 | 11.8 | NIL | NIL | 16 | 11 | 21 |
| 23 | 1.41 | ND | ND | 17 | 12 | 22 |
| 24 | 10.8 | — | 6.18 | 24 | 15 | 14 |
| 25 | NIL | ND | ND | 04 | 10 | 33 |
| 26 | NIL | ND | ND | 37 | 28 | 39 |
| 27 | 38.0 | NIL | NIL | 25 | 22 | 20 |
| 28 | 4.41 | ND | ND | 40 | 26 | 17 |
| 29 | 6.85 | NIL | NIL | 33 | 27 | 27 |
| 30 | 20.0 | — | 11.3 | 27 | 25 | 30 |
| 31 | 33.1 | NIL | NIL | — | 03 | — |
| 32 | 47.0 | — | 2.77 | 22 | 15 | 29 |
| 33 | 5.03 | ND | ND | 22 | 21 | 16 |
| 34 | 21.1 | — | 23.0 | 26 | 20 | 18 |
| 35 | 23.8 | — | 11.6 | 13 | 09 | 13 |
| 43 | NIL | ND | ND | 04 | 14 | 31 |
| 44 | NIL | ND | ND | 06 | 13 | 19 |
| 45 | 0.13 | ND | ND | 23 | 21 | 14 |
| 46 | 13.4 | 11.8 | 7.18 | 13 | 20 | 20 |

Evaluation of Antihyperglycemic and Antidyslipidemic Activity in db/db Mice

The db/db mouse is a well-characterized model of type H diabetes. The background for the db/db mouse is the C57BL/Ks strain. The major deficiency of the C57BL/KsBom-db mouse (db/db) is lack of a functional leptin receptor. This leads to defective leptin signaling and a complete lack of feedback from leptin. Both hypothalamic NPY content and secretion are consequently elevated, and this result in hyperphagia and decreased energy expenditure, obesity, insulin-resistance, hyperinsulinaemia, hyperglycemia and dyslipidemia. The db/db mouse develops NIDDM from around week 10. The disease is stable until week 20, where destruction of pancreatic β-cells can be recognized clinically as decreasing levels of plasma insulin and very severe hyperglycemia. The male mice are more diabetic than female and will normally die earlier. The advantage of using male mice for experimental purposes is that the fluctuations in plasma parameters are less than in the females where the estrogen cycle affects the clinical diabetes mellitus. The optimal age of db/db mice used for experiments will be from week 12 to 18 when they have developed NIDDM with diabetic dyslipidemia but still have functional β-cells in the pancreas. C57BL/KsBom-db mice 12-18 weeks, 40-50 g bred in the animal house of CDRI, Lucknow. 10 male mice were used in the experiments. The mice were housed in groups of 5 individuals in a room controlled for temperature (23±2° C.) and 12/12 hours light/dark cycle (lights on at 6.00 am). Body weight was measured daily from day 1 to day 10. All animals had free access to fresh water and to normal chow except on the days of the postprandial protocol day 6 and during the overnight fast before the OGTT on day 10. Blood glucose was checked every morning up till day 5. On day 6 postprandial protocol was employed, in this method blood glucose was checked at −0.30 min and 0 h. Test compounds were given to the treatment group whereas control group received only gum acacia (1.0%); the blood glucose was again checked at 1, 2, 3, 4 and 6 h post test compound treatment. Finally on day 10 an oral glucose tolerance test (OGTT) was performed after an overnight fasting. Blood glucose was measured at −0.30 min and test drugs were fed, blood glucose was again measured at 0.0 min post treatment, at this juncture glucose solution was given at a dose of 3 gm/kg to all the groups including control group; the profile of blood glucose was checked at 30 min, 60 min, 90 min and 120 min post glucose administration. Quantitative glucose tolerance of each animal was calculated by Area Under Curve (AUC) method (Prism Software). Comparing the AUC of experimental and control groups determined the percentage antihyperglycemic activity. Statistical comparison was made by Dunnett's test.

Lipid Cholesterol

Cholesterol and triglycerides were estimated using the same procedures as given above.

HDL-Cholesterol

HDL-Cholesterol was estimated using the kit provided by the Roche Diagnostics. Cholestest N HDL is a liquid reagent that directly measures the HDL-cholesterol concentration in serum by a new method that is based on the selective solubilising effect of proprietary detergent to the different lipoproteins. In the assay system, only HDL is solubilised by a special detergent; other lipoproteins are not disturbed. After HDL is selectively disrupted, HDL cholesterol is measured enzymatically (Gordon, T.; Casstelli, W. P.; Hjortland, M. C.; Kannel, W. B.; Dawber, T. R. High density lipoproteins as a protective factor against coronary heart disease, Am. J. Med. 1977, 62, 707-714.).

TABLE 4

Antihyperglycemic activity in db/db mice

| | % Fall in blood glucose levels | |
|---|---|---|
| Compound number | 6 days | 10 days |
| 18 | 29.9 | 18.9 |
| 34 | NIL | 32.0 |
| 46 | 1.76 | 23.1 |

TABLE 5

Antidyslipidemic activity in db/db mice

| | % Fall in lipid levels | | |
|---|---|---|---|
| Compound number | TG | Chol. | HDL |
| 18 | +5.20 | 1.36 | 11.8 |
| 34 | +7.44 | 40.3 | +1.76 |
| 46 | 6.76 | 18.9 | 21.4 |

Results:

The activity of chalcones in SLM and STZ models are given in table 3 and compounds 18 and 34 showed significant results. Compound 46 in this series was also taken up for detailed study and showed significant lowering of blood glucose in db/db mice (Tables 3-5).

We claim:

1. A compound having formula (I) or a pharmaceutically acceptable salt thereof:

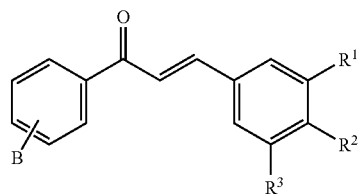

I wherein $R^1$, $R^2$ and $R^3$ are selected from the group consisting of H, OH, O-alkyl, O-phenyl, and O-substituted phenyl;

B represents Ar—Z—O or RO;

where Z is an alkane having up to 5 carbon atoms;

R is substituted propanol amino, wherein the substituted groups are selected from the group consisting of t-butyl, n-butyl, i-butyl, i-propyl, 4-phenyl piperazin-1-yl, 4-(2-methoxyphenyl)-piperazin-1-yl and 3,4-dimethoxy phenethyl; and Ar is thiazolidinedione methylene phenoxy.

2. A compound selected from the group consisting of (i) 3,4-Dimethoxy-4'-[2-hydroxy-3-(4-phenylpiperazin-1-yl)-propoxy]-chalcone;

(ii) 4'-[3-tert-Butylamino-2-hydroxy-propoxy]-3,4-dimethoxy-chalcone;

(iii) 4'-[2-Hydroxy-3-(4-phenylpiperazin-1-yl)-propoxy]-4-methoxy-chalcone;

(iv) 4'-[3-iso-Butylamino-2-hydroxy-propoxy]-4-methoxy-chalcone;

(v) 4'-[3-tert-Butylamino-2-hydroxy-propoxy]-4-methoxy-chalcone;

(vi) 4'-[2-Hydroxy-3-iso-propylamino-propoxy]-4-methoxy-chalcone;

(vii) 4'-[2-Hydroxy-3-{4-(2-methoxyphenyl)-piperazin-1-yl}-propoxy]-4-methoxy-chalcone;

(viii) 4'-[3-{2-(3,4-Dimethoxyphenyl)-ethylamino}-2-hydroxy-propoxy]-4-methoxy-chalcone;

(ix) 4'-[2-Hydroxy-3-methylamino-propoxy]-4-methoxy-chalcone;

(x) 4'-[3-n-Butylamino-2-hydroxy-propoxy]-4-methoxy-chalcone;

(xi) 3'-[2-Hydroxy-3-(4-phenylpiperazin-1-yl)-propoxy]-4-methoxy-chalcone;

(xii) 3'-[2-Hydroxy-3-iso-propylamino-propoxy]-4-methoxy-chalcone;

(xiii) 3'-[3-tert-Butylamino-2-hydroxy-propoxy]-4-methoxy-chalcone;

(xiv) 2'-[3-n-Butylamino-2-hydroxy-propoxy]-4-methoxy-chalcone;

(xv) 2'-[2-Hydroxy-3-iso-propylamino-propoxy]-4-methoxy-chalcone;

(xvi) 4'-[2-Hydroxy-3-(4-phenylpiperazin-1-yl)-propoxy]-3,4-methylenedioxy-chalcone;

(xvii) 4'-[3-tert-Butylamino-2-hydroxy-propoxy]-3,4-methylenedioxy-chalcone; and (xviii) 4'-[3-iso-Butylamino-2-hydroxy-propoxy]-3,4-methylenedioxy-chalcone, or a pharmaceutically acceptable salt thereof.

3. A compound selected from the group consisting of (i) 4-Methoxy-3'-{4-[4-(thiazol id in-2,4-dione-5-ylidinemethyl)-phenoxy]-butoxy}-chalcone;

(ii) 4-Methoxy-3'-{5-[4-(thiazolidin-2,4-dione-5-ylidinemethyl)-phenoxy]-pentyloxy}-chalcone;

(iii) 3,4-Methylenedioxy-3'-{4-[4-(thiazolidin-2,4-dione-5-ylidinemethyl)-phenoxy]-butoxy}-chalcone; and (iv) 3,4-Methylenedioxy-3'-{5-[4-(thiazolidin-2,4-dione-5-ylidinemethyl)-phenoxy]-pentyloxy}-chalcone, or a pharmaceutically acceptable salt thereof.

4. The compound as claimed in claim 1 having a formula (18):

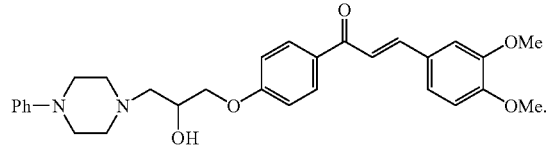

5. The compound as claimed in claim 2 having a formula (34):

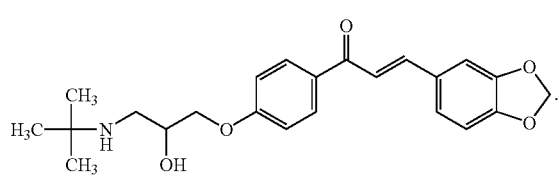

6. The compound as claimed in claim 3 having a formula (46):

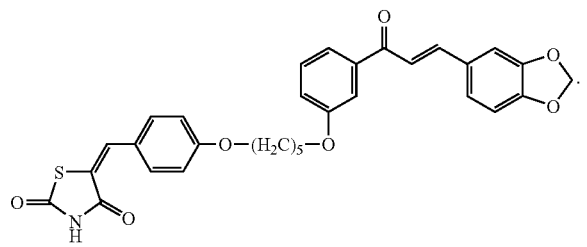

7. A composition comprising a compound of formula I or a pharmaceutically acceptable salt thereof:

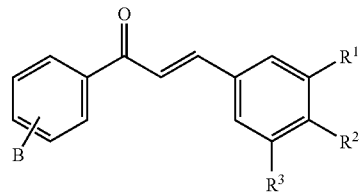

wherein
$R^1$, $R^2$ and $R^3$ are independently selected from the group consisting of H, OH, O-alkyl, O-phenyl, and O-substituted phenyl;
B represents Ar—Z—O or RO;
where Z is an alkane having up to 5 carbon atoms;
R is substituted propanol amino, wherein substituted amino groups are selected from the group consisting of t-butyl, n-butyl, i-butyl, i-propyl, 4-phenyl piperazin-1-yl, 4-(2-methoxyphenyl)-piperazin-1-yl and 3,4-dimethoxy phenethyl; and
Ar is thiazolidinedione methylene phenoxy;

with a pharmaceutically acceptable carrier or diluent thereof.

8. A composition comprising a compound of formula I or a pharmaceutically acceptable salt thereof:

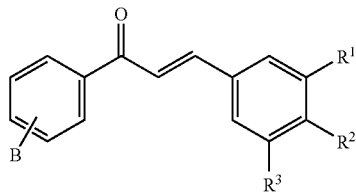

wherein
$R^1$, $R^2$ and $R^3$ are independently selected from the group consisting of H, OH, O-alkyl, O-phenyl, and O-substituted phenyl;
B represents Ar—Z—O or RO;
where Z is an alkane having up to 5 carbon atoms;
R is substituted propanol amino, wherein the substituted groups are selected from the group consisting of t-butyl, n-butyl, i-butyl, i-propyl, 4-phenyl piperazin-1-yl, 4-(2-methoxyphenyl)-piperazin-1-yl and 3,4-dimethoxy phenethyl; and
Ar is thiazolidinedione methylene phenoxy;
along with a lipid lowering agent and/or a sugar lowering.

9. A process for preparing a compound of formula I as claimed in claim 1, comprising the steps of:
(i) reacting hydroxy acetophenone and substituted benzaldehyde using aqueous sodium hydroxide in methanol at room temperature to obtain chalcones, wherein the benzaldehyde is substituted with one or more substituents selected from the group consisting of H, OH, O-alkyl, O-phenyl, and O-substituted phenyl;
(ii) reacting chalcones obtained in step (i) with epichlorohydrin using sodium hydride as base in dry dimethyl formamide to obtain an epoxide; and
(iii) heating the epoxide obtained in step (ii) under reflux at room temperature with suitable amines which are selected from the group consisting of t-butyl amine, n-butyl amine, i-butyl amine, i-propyl amine, 4-phenyl piperazine 4-(2 methoxyphenyl)-piperazine and 3,4-dimethoxy phenethyl amine, in methanol to yield corresponding substituted propanolamines.

10. A process for preparing a compound of formula I as claimed in claim 1 comprising the steps of:
(i) reacting chalcone with dibromo alkane in the presence of $K_2CO_3$ and acetone at room temperature to get bromo alkoxy chalcone; and
(ii) reacting bromo alkoxy chalcone obtained in step (i) with 4-(Thiazolidin-2,4-dione-5-ylidinemethyl)-phenol, in the presence of $K_2CO_3$ and dimethyl formamide at room temperature to obtain the corresponding chalcone derived thiazolidinediones.

11. A method of treating type II diabetes in mammals, said method comprising the step of administering a pharmaceutically effective amount of a compound of formula I, or pharmaceutical salts thereof, optionally with other antidiabetic and antidyslipidemic agents:

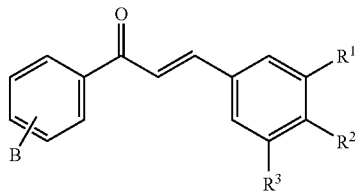

wherein

R¹, R² and R³ are selected from the group consisting of H, OH, O-alkyl, O-phenyl, and O-substituted phenyl;

B represents Ar—Z—O or RO;

where Z is an alkane having up to 5 carbon atoms;

R is substituted propanol amino, wherein the substituted groups are selected from the group consisting of t-butyl, n-butyl, i-butyl, i-propyl, 4-phenyl piperazin-1-yl, 4-(2-methoxyphenyl)-piperazin-1-yl and 3,4-dimethoxy phenethyl; and Ar is thiazolidinedione methylene phenoxy.

12. The method as claimed in claim 11, for treating type II diabetes in mammals, said method comprising the step of administering a pharmaceutically effective amount of a compound of formula (18) or a pharmaceutical salt thereof, optionally with other antidiabetic and antidyslipidemic agents:

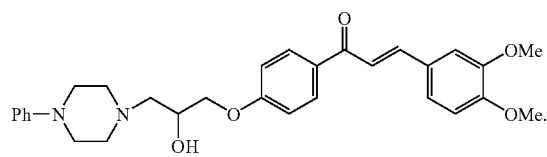

13. A method for treating type II diabetes in mammals, said method comprising the step of administering a pharmaceutically effective amount of a compound of formula (34) or a pharmaceutical salt thereof, optionally with other antidiabetic and antidyslipidemic agents:

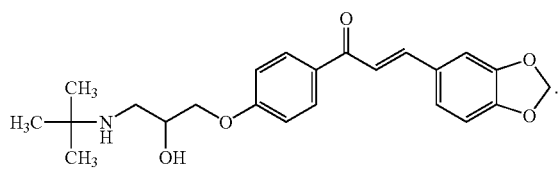

14. A method for treating type II diabetes in mammals, said method comprising the step of administering a pharmaceutically effective amount of a compound of formula (46) or a pharmaceutical salt thereof, optionally with other antidiabetic and antidyslipidemic agents:

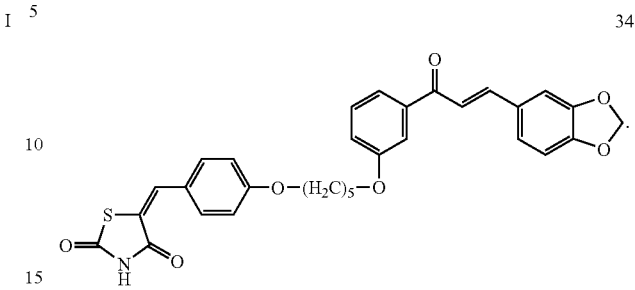

15. A method of treating hyperlipidemic conditions in mammals, said method comprising the step of administering a pharmaceutically effective amount of a compound of formula I, or pharmaceutical salts thereof, optionally with other antidiabetic and antidyslipidemic agents:

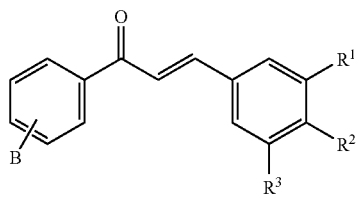

wherein

R¹, R² and R³ are selected from the group consisting of H, OH, O-alkyl, O-phenyl, and O-substituted phenyl;

B represents Ar—Z—O or RO;

where Z is an alkane having up to 5 carbon atoms;

R is substituted propanol amino, wherein the substituted groups are selected from t-butyl, n-butyl, i-butyl, i-propyl, 4-phenyl piperazin-1-yl, 4-(2-methoxyphenyl)-piperazin-1-yl and 3,4-dimethoxy phenethyl; and Ar is thiazolidinedione methylene phenoxy.

16. The method as claimed in claim 15, for treating hyperlipidemic conditions in mammals, said method comprising the step of administering a pharmaceutically effective amount of a compound of formula (18) or a pharmaceutical salt thereof, optionally with other antidiabetic and antidyslipidemic agents:

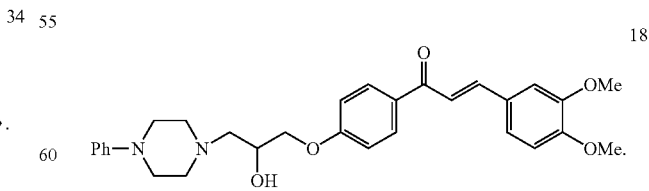

17. The method as claimed in claim 15, for treating hyperlipidemic conditions in mammals, said method comprising the step of administering a pharmaceutically effective amount of a compound of formula (34) or a pharmaceutical salt thereof, optionally with other antidiabetic and antidvslipidemic agents:

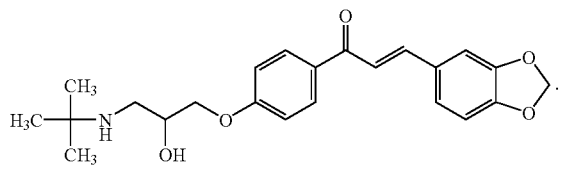

18. A method for treating hyperlipidemic conditions in mammals, said method comprising the step of administering a pharmaceutically effective amount of a compound of formula (46) or a pharmaceutical salt thereof, optionally with other antidiabetic and antidvslipidemic agents:

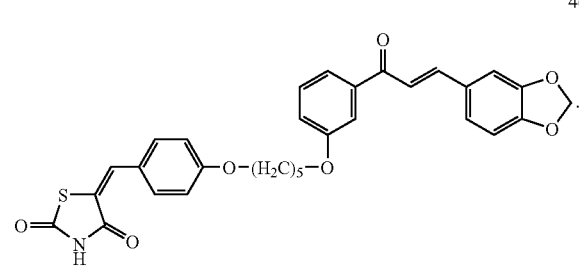

19. A method of treating macrovascular conditions selected from the group consisting of retinopathy and nephropathy in mammals, said method comprising the step of administering a pharmaceutically effective amount of a compound of formula I, or pharmaceutical salts thereof, optionally with other antidiabetic and antidyslipidemic agents:

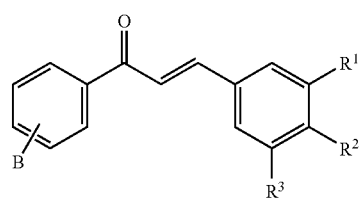

wherein
$R^1$, $R^2$ and $R^3$ are selected from the group consisting of H, OH, O-alkyl, O-phenyl, and O-substituted phenyl;
B represents Ar—Z—O or RO;
where Z is an alkane having up to 5 carbon atoms;
R is substituted propanol amino, wherein the substituted groups are selected from t-butyl, n-butyl, i-butyl, i-propyl, 4-phenyl piperazin-1-yl, 4-(2-methoxyphenyl)-piperazin-1-yl and 3,4-dimethoxy phenethyl; and
Ar is thiazolidinedione methylene phenoxy.

20. The method as claimed in claim 19, for treating macrovascular conditions selected from the group consisting of retinopathy and nephropathy in mammals, said method comprising the step of administering a pharmaceutically effective amount of a compound of formula (18) or a pharmaceutical salt thereof, optionally with other antidiabetic and antidvslipidemic agents:

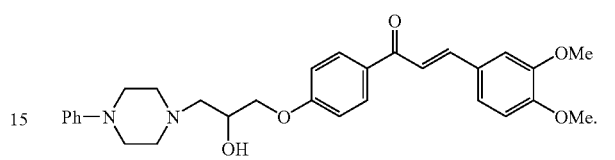

21. A method for treating macrovascular conditions selected from the group consisting of retinopathy and nephropathy in mammals, said method comprising the step of administering a pharmaceutically effective amount of a compound of formula (34) or a pharmaceutical salt thereof, optionally with other antidiabetic and antidyslipidemic agents:

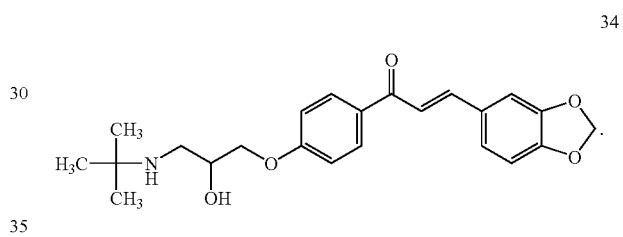

22. A method for treating macrovascular conditions selected from the group consisting of retinopathy and nephropathy in mammals, said method comprising the step of administering a pharmaceutically effective amount of a compound of formula (46) or a pharmaceutical salt thereof, optionally with other antidiabetic and antidvslipidemic agents:

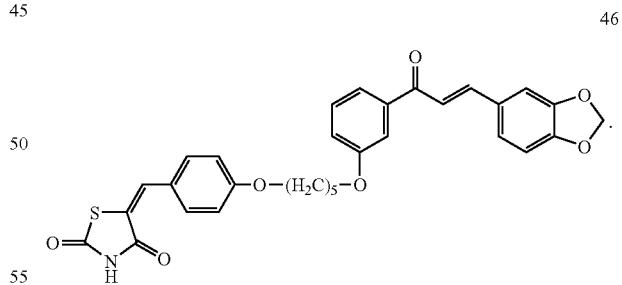

23. The composition as claimed in claim 8, comprising the lipid lowering agent and a sugar lowering agent.

* * * * *